(12) United States Patent
Barres et al.

(10) Patent No.: US 8,895,507 B2
(45) Date of Patent: Nov. 25, 2014

(54) MODULATION OF SYNAPTOGENESIS

(75) Inventors: Ben A. Barres, Palo Alto, CA (US); Cagla Eroglu, Burlingame, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 962 days.

(21) Appl. No.: 12/148,166

(22) Filed: Apr. 16, 2008

(65) Prior Publication Data

US 2009/0029909 A1 Jan. 29, 2009

Related U.S. Application Data

(60) Provisional application No. 60/923,940, filed on Apr. 16, 2007.

(51) Int. Cl.
| | | |
|---|---|---|
| *C07K 14/475* | (2006.01) | |
| *A61K 38/18* | (2006.01) | |
| *G01N 33/50* | (2006.01) | |
| *A61K 38/17* | (2006.01) | |
| *C07K 14/47* | (2006.01) | |
| *A61K 38/39* | (2006.01) | |

(52) U.S. Cl.
CPC ........ *A61K 38/1709* (2013.01); *G01N 33/5058* (2013.01); *C07K 14/4702* (2013.01); *G01N 33/5032* (2013.01); *G01N 2333/4727* (2013.01); *A61K 38/39* (2013.01)
USPC .......................................... 514/8.3; 530/395

(58) Field of Classification Search
None
See application file for complete search history.

(56) References Cited

U.S. PATENT DOCUMENTS

| | | |
|---|---|---|
| 2002/0098514 A1 | 7/2002 | Heichman |
| 2004/0106646 A1 | 6/2004 | Takayama et al. |
| 2005/0071088 A1 | 3/2005 | Landfield et al. |
| 2006/0019880 A1 | 1/2006 | Barres et al. |

OTHER PUBLICATIONS

Burns et al., Neuron, 7(2): 209-220, 1991.*
Pollerberg et al., Dev Biol., 165(2): 60-687, 1994.*
Li et al., Biochem Biophys Res Comm., 339: 797-804, 2006.*
Information Hyperlinked over Proteins (iHOP) datasheet for SPARCL-1 (hevin) [online; retrieved on Dec. 2, 2009]. Retrieved from: <http://www.ihop-net.org/UniPub/iHOP/>.*
Weaver et al., Journal of Biological Chemistry, 285(8): Feb. 19, 2010.*
Gutierrez-Fernandez et al., J Cell Mol Med., 16(10): 2280-2290, 2012.*
Fu et al., Invest Ophthalmol & Vis Sci., 52(11):8374-8380, 2011.*
Bradshaw; et al., "SPARC, a matricellular protein that functions in cellular differentiation and tissue response to injury", The Journal of Clinical Investigation, May 2001, 107(9):1049-54.
Brekken; et al., "SPARC, a matricellular protein: at the crossroads of cell-matrix communication", Matrix Biology, 2001, 19:815-27.
Christopherson; et al., "Thrombospondins Are Astrocyte-Secreted Proteins that Promote CNS Synaptogenesis", Cell, Feb. 11, 2005, 120:421-433.
Elmariah; et al., "Astrocytes Regulate Inhibitory Synapse Formation via Trk-Mediated Modulation of Postsynaptic GABA(subscript A) Receptors", The Journal of Neuroscience, Apr. 6, 2005, 25(14):3638-3650.
Girard; et al., "Cloning from Purified High Endothelial Venule Cells of Hevin, a Close Relative of the Antiadhesive Extracellular Matrix Protein SPARC", Immunity, Jan. 1995, 2:113-123.
Meyer-Franke; et al., "Characterization of the Signaling Interactions That Promote the Survival and Growth of Developing Retinal Ganglion Cells in Culture", Neuron, Oct. 1995, 15:805-819.
Ullian; et al., "Control of Synapse Number by Glia", Science, Jan. 26, 2001, 291:657-661.
Ullian; et al., "Schwann cells and astrocytes induce synapse formation by spinal motor neurons in culture", Mol Cell Neurosci, Feb. 2004, 25(2):241-251.
Young; et al., "Structure and Expression of Osteonectin mRNA in Human Tissue", Connective Tissue Research, 1990, 24:17-28.

\* cited by examiner

*Primary Examiner* — Daniel E Kolker
*Assistant Examiner* — Stacey N MacFarlane
(74) *Attorney, Agent, or Firm* — Bozicevic, Field & Francis LLP; Pamela J. Sherwood

(57) ABSTRACT

Soluble proteins, e.g. Hevin, can trigger synapse formation; and other soluble proteins, e.g. SPARC antagonize this activity. Such proteins are synthesized in vitro and in vivo by astrocytes. Methods are provided for protecting or treating an individual suffering from adverse effects of deficits in synaptogenesis, or from undesirably active synaptogenesis.

4 Claims, 8 Drawing Sheets
(4 of 8 Drawing Sheet(s) Filed in Color)

FIGURE 2
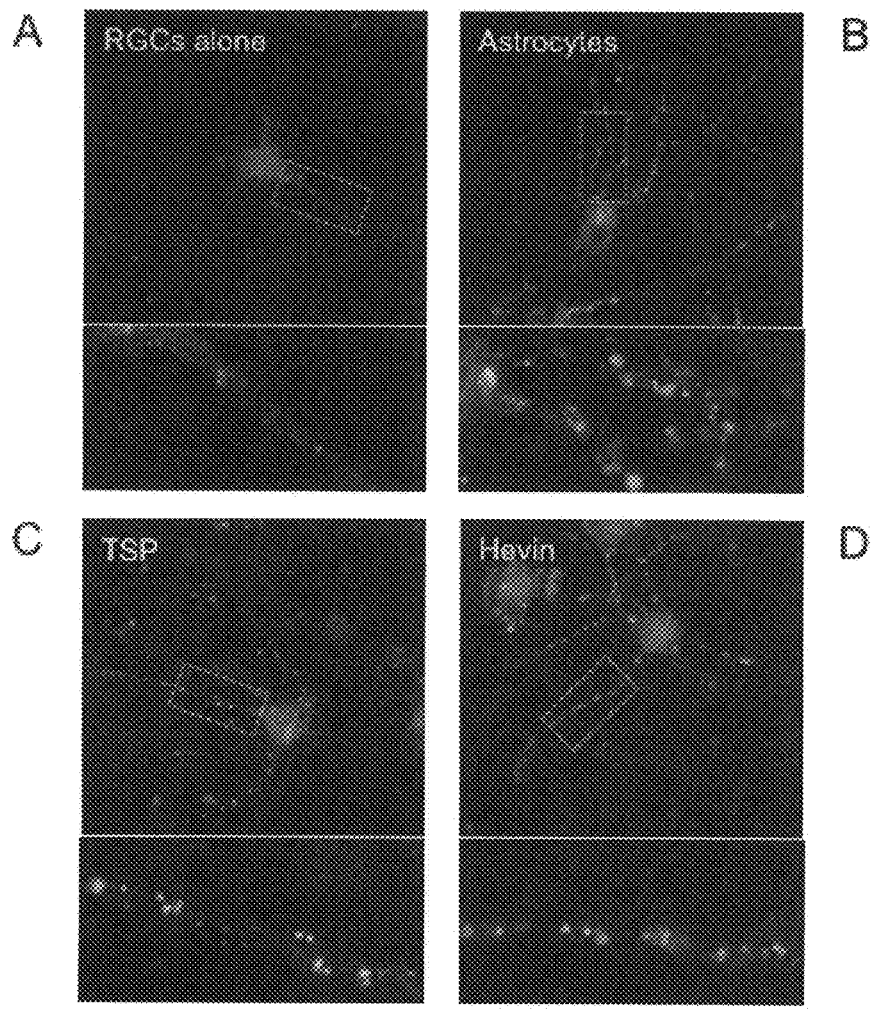
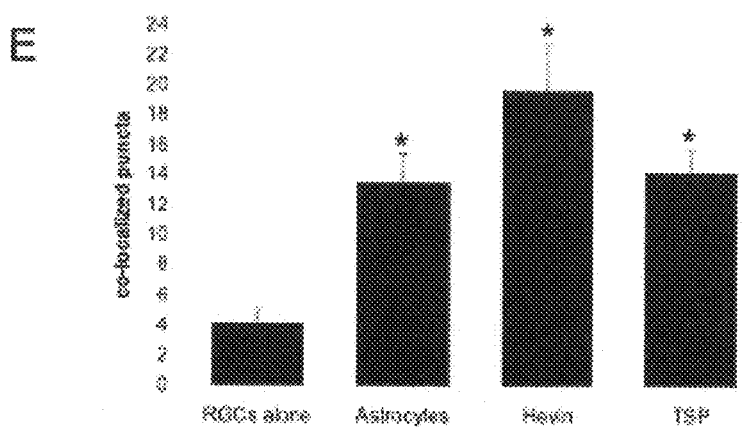

FIGURE 7
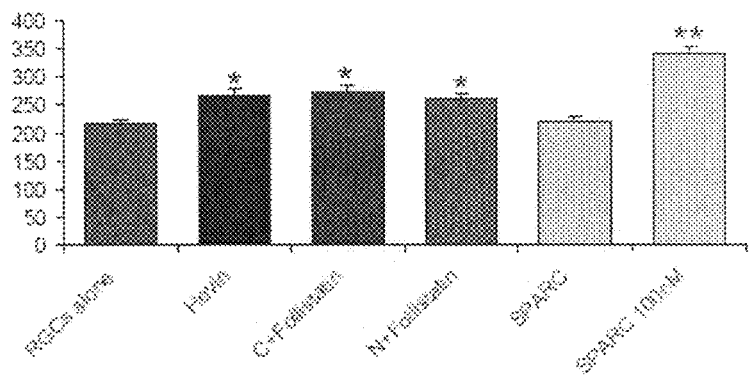
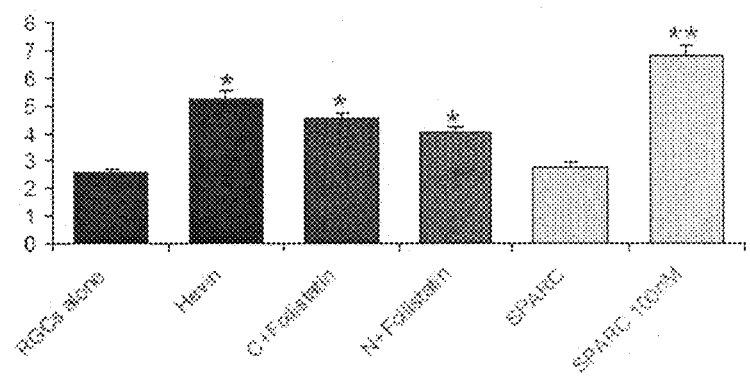

SEQUENCE LISTING

```
<160> NUMBER OF SEQ ID NOS: 5

<210> SEQ ID NO 1
<211> LENGTH: 664
<212> TYPE: PRT
<213> ORGANISM: homo sapien

<400> SEQUENCE: 1

Met Lys Thr Gly Pro Phe Phe Leu Cys Leu Leu Gly Thr Ala Ala Ala
 1               5                  10                  15

Ile Pro Thr Asn Ala Arg Leu Leu Ser Asp His Ser Lys Pro Thr Ala
            20                  25                  30

Glu Thr Val Ala Pro Asp Asn Thr Ala Ile Pro Ser Leu Trp Ala Glu
        35                  40                  45

Ala Glu Glu Asn Glu Lys Glu Thr Ala Val Ser Thr Glu Asp Asp Ser
    50                  55                  60

His His Lys Ala Glu Lys Ser Ser Val Leu Lys Ser Lys Glu Glu Ser
65                  70                  75                  80

His Glu Gln Ser Ala Glu Gln Gly Lys Ser Ser Ser Gln Glu Leu Gly
                85                  90                  95

Leu Lys Asp Gln Glu Asp Ser Asp Gly His Leu Ser Val Asn Leu Glu
            100                 105                 110

Tyr Ala Pro Thr Glu Gly Thr Leu Asp Ile Lys Glu Asp Met Ile Glu
        115                 120                 125

Pro Gln Glu Lys Lys Leu Ser Glu Asn Thr Asp Phe Leu Ala Pro Gly
    130                 135                 140

Val Ser Ser Phe Thr Asp Ser Asn Gln Gln Glu Ser Ile Thr Lys Arg
145                 150                 155                 160

Glu Glu Asn Gln Glu Gln Pro Arg Asn Tyr Ser His His Gln Leu Asn
                165                 170                 175

Arg Ser Ser Lys His Ser Gln Gly Leu Arg Asp Gln Gly Asn Gln Glu
            180                 185                 190

Gln Asp Pro Asn Ile Ser Asn Gly Glu Glu Glu Glu Lys Glu Pro
        195                 200                 205

Gly Glu Val Gly Thr His Asn Asp Asn Gln Glu Arg Lys Thr Glu Leu
    210                 215                 220

Pro Arg Glu His Ala Asn Ser Lys Gln Glu Glu Asp Asn Thr Gln Ser
225                 230                 235                 240

Asp Asp Ile Leu Glu Glu Ser Asp Gln Pro Thr Gln Val Ser Lys Met
                245                 250                 255

Gln Glu Asp Glu Phe Asp Gln Gly Asn Gln Glu Gln Glu Asp Asn Ser
```

```
                260                 265                 270
Asn Ala Glu Met Glu Glu Asn Ala Ser Asn Val Asn Lys His Ile
                275                 280                 285
Gln Glu Thr Glu Trp Gln Ser Gln Glu Gly Lys Thr Gly Leu Glu Ala
                290                 295                 300
Ile Ser Asn His Lys Glu Thr Glu Lys Thr Val Ser Glu Ala Leu
305                 310                 315                 320
Leu Met Glu Pro Thr Asp Asp Gly Asn Thr Thr Pro Arg Asn His Gly
                    325                 330                 335
Val Asp Asp Asp Gly Asp Asp Gly Asp Asp Gly Thr Asp Gly
                340                 345                 350
Pro Arg His Ser Ala Ser Asp Asp Tyr Phe Ile Pro Ser Gln Ala Phe
                355                 360                 365
Leu Glu Ala Glu Arg Ala Gln Ser Ile Ala Tyr His Leu Lys Ile Glu
                370                 375                 380
Glu Gln Arg Glu Lys Val His Glu Asn Glu Asn Ile Gly Thr Thr Glu
385                 390                 395                 400
Pro Gly Glu His Gln Glu Ala Lys Lys Ala Glu Asn Ser Ser Asn Glu
                    405                 410                 415
Glu Glu Thr Ser Ser Glu Gly Asn Met Arg Val His Ala Val Asp Ser
                420                 425                 430
Cys Met Ser Phe Gln Cys Lys Arg Gly His Ile Cys Lys Ala Asp Gln
                435                 440                 445
Gln Gly Lys Pro His Cys Val Cys Gln Asp Pro Val Thr Cys Pro Pro
                450                 455                 460
Thr Lys Pro Leu Asp Gln Val Cys Gly Thr Asp Asn Gln Thr Tyr Ala
465                 470                 475                 480
Ser Ser Cys His Leu Phe Ala Thr Lys Cys Arg Leu Glu Gly Thr Lys
                    485                 490                 495
Lys Gly His Gln Leu Gln Leu Asp Tyr Phe Gly Ala Cys Lys Ser Ile
                500                 505                 510
Pro Thr Cys Thr Asp Phe Glu Val Ile Gln Phe Pro Leu Arg Met Arg
                515                 520                 525
Asp Trp Leu Lys Asn Ile Leu Met Gln Leu Tyr Glu Ala Asn Ser Glu
                530                 535                 540
His Ala Gly Tyr Leu Asn Glu Lys Gln Arg Asn Lys Val Lys Lys Ile
545                 550                 555                 560
Tyr Leu Asp Glu Lys Arg Leu Leu Ala Gly Asp His Pro Ile Asp Leu
                    565                 570                 575
Leu Leu Arg Asp Phe Lys Lys Asn Tyr His Met Tyr Val Tyr Pro Val
                580                 585                 590
His Trp Gln Phe Ser Glu Leu Asp Gln His Pro Met Asp Arg Val Leu
                595                 600                 605
Thr His Ser Glu Leu Ala Pro Leu Arg Ala Ser Leu Val Pro Met Glu
                610                 615                 620
His Cys Ile Thr Arg Phe Phe Glu Glu Cys Asp Pro Asn Lys Asp Lys
625                 630                 635                 640
His Ile Thr Leu Lys Glu Trp Gly His Cys Phe Gly Ile Lys Glu Glu
                    645                 650                 655
Asp Ile Asp Glu Asn Leu Leu Phe
                660

<210> SEQ ID NO 2
```

<211> LENGTH: 2806
<212> TYPE: DNA
<213> ORGANISM: homo sapien

<400> SEQUENCE: 2

| | | | | | |
|---|---|---|---|---|---|
| gcatgagagg | ccagcctgcc | agggaaatcc | aggaatctgc | aacaaaaacg | atgacagtct | 60 |
| gaaatactct | ctggtgccaa | cctccaaatt | ctcgtctgtc | acttcagacc | cccactagtt | 120 |
| gacagagcag | cagaatatca | actccagtag | acttgaatgt | gcctctgggc | aaagaagcag | 180 |
| agctaacgag | gaaagggatt | taaagagttt | ttcttgggtg | tttgtcaaac | ttttattccc | 240 |
| tgtctgtgtg | cagaggggat | tcaacttcaa | ttttctgcag | tggctctggg | tccagcccct | 300 |
| tacttaaaga | tctggaaagc | atgaagactg | ggcctttttt | cctatgtctc | ttgggaactg | 360 |
| cagctgcaat | cccgacaaat | gcaagattat | tatctgatca | ttccaaacca | actgctgaaa | 420 |
| cggtagcacc | tgacaacact | gcaatcccca | gtttatgggc | tgaagctgaa | gaaaatgaaa | 480 |
| aagaaacagc | agtatccaca | gaagacgatt | cccaccataa | ggctgaaaaa | tcatcagtac | 540 |
| taaagtcaaa | agaggaaagc | catgaacagt | cagcagaaca | gggcaagagt | tctagccaag | 600 |
| agctgggatt | gaaggatcaa | gaggacagtg | atggtcactt | aagtgtgaat | ttggagtatg | 660 |
| caccaactga | aggtacattg | gacataaaag | aagatatgat | tgagcctcag | gagaaaaaac | 720 |
| tctcagagaa | cactgatttt | ttggctcctg | gtgttagttc | cttcacagat | tctaaccaac | 780 |
| aagaaagtat | cacaaagaga | gaggaaaaacc | aagaacaacc | tagaaattat | tcacatcatc | 840 |
| agttgaacag | gagcagtaaa | catagccaag | gcctaaggga | tcaaggaaac | caagagcagg | 900 |
| atccaaatat | ttccaatgga | gaagaggaag | aagaaaaaga | gccaggtgaa | gttggtaccc | 960 |
| acaatgataa | ccaagaaaga | aagacagaat | tgcccaggga | gcatgctaac | agcaagcagg | 1020 |
| aggaagacaa | tacccaatct | gatgatattt | tggaagagtc | tgatcaacca | actcaagtaa | 1080 |
| gcaagatgca | ggaggatgaa | tttgatcagg | gtaaccaaga | acaagaagat | aactccaatg | 1140 |
| cagaaatgga | gaggaaaat | gcatcgaacg | tcaataagca | cattcaagaa | actgaatggc | 1200 |
| agagtcaaga | gggtaaaact | ggcctagaag | ctatcagcaa | ccacaaagag | acagaagaaa | 1260 |
| agactgtttc | tgaggctctg | ctcatggaac | ctactgatga | tggtaatacc | acgcccagaa | 1320 |
| atcatggagt | tgatgatgat | ggcgatgatg | atggcgatga | tggcggcact | gatggcccca | 1380 |
| ggcacagtgc | aagtgatgac | tacttcatcc | caagccaggc | cttctggag | ccgagagag | 1440 |
| ctcaatccat | tgcctatcac | ctcaaaattg | aggagcaaag | agaaaaagta | catgaaaatg | 1500 |
| aaaatatagg | taccactgag | cctggagagc | accaagaggc | caagaaagca | gagaactcat | 1560 |
| caaatgagga | ggaaacgtca | agtgaaggca | acatgagggt | gcatgctgtg | gattcttgca | 1620 |
| tgagcttcca | gtgtaaaaga | ggccacatct | gtaaggcaga | ccaacaggga | aaacctcact | 1680 |
| gtgtctgcca | ggatccagtg | acttgtcctc | caacaaaacc | ccttgatcaa | gtttgtggca | 1740 |
| ctgacaatca | gacctatgct | agttcctgtc | atctattcgc | tactaaatgc | agactggagg | 1800 |
| ggaccaaaaa | ggggcatcaa | ctccagctgg | attattttgg | agcctgcaaa | tctattccta | 1860 |
| cttgtacgga | ctttgaagtg | attcagtttc | ctctacggat | gagagactgg | ctcaagaata | 1920 |
| tcctcatgca | gctttatgaa | gccaactctg | aacatgctgg | ttatctaaat | gagaagcaga | 1980 |
| gaaataaagt | caagaaaatt | tacctggatg | aaaagagggct | tttggctggg | gaccatccca | 2040 |
| ttgatcttct | cttaagggac | tttaagaaaa | actaccacat | gtatgtgtat | cctgtgcact | 2100 |
| ggcagtttag | tgaacttgac | caacacccta | tggatagagt | cttgacacat | tctgaacttg | 2160 |
| ctcctctgcg | agcatctctg | gtgcccatgg | aacactgcat | aacccgtttc | tttgaggagt | 2220 |

```
gtgaccccaa caaggataag cacatcaccc tgaaggagtg gggccactgc tttggaatta    2280
aagaagagga catagatgaa aatctcttgt tttgaacgaa gattttaaag aactcaactt    2340
tccagcatcc tcctctgttc taaccacttc agaaatatat gcagctgtga tacttgtaga    2400
tttatattta gcaaaatgtt agcatgtatg acaagacaat gagagtaatt gcttgacaac    2460
aacctatgca ccaggtattt aacattaact ttggaaacaa aaatgtacaa ttaagtaaag    2520
tcaacatatg caaaatactg tacattgtga acagaagttt aattcatagt aatttcactc    2580
tctgcattga cttatgagat aattaatgat taaactatta atgataaaaa taatgcattt    2640
gtattgttca taatatcatg tgcacttcaa gaaaatggaa tgctactctt ttgtggttta    2700
cgtgtattat tttcaatatc ttaataccct aataaagagt ccataaaaat ccaaaaaaaa    2760
aaaaaaaaaa aaaaaaaaaa aaaaaaaaaa aaaaaaaaa aaaaa                     2806
```

<210> SEQ ID NO 3
<211> LENGTH: 303
<212> TYPE: PRT
<213> ORGANISM: homo sapien

<400> SEQUENCE: 3

```
Met Arg Ala Trp Ile Phe Phe Leu Leu Cys Leu Ala Gly Arg Ala Leu
1               5                   10                  15

Ala Ala Pro Gln Gln Glu Ala Leu Pro Asp Glu Thr Glu Val Val Glu
            20                  25                  30

Glu Thr Val Ala Glu Val Thr Glu Val Ser Val Gly Ala Asn Pro Val
        35                  40                  45

Gln Val Glu Val Gly Glu Phe Asp Asp Gly Ala Glu Glu Thr Glu Glu
    50                  55                  60

Glu Val Val Ala Glu Asn Pro Cys Gln Asn His His Cys Lys His Gly
65                  70                  75                  80

Lys Val Cys Glu Leu Asp Glu Asn Asn Thr Pro Met Cys Val Cys Gln
                85                  90                  95

Asp Pro Thr Ser Cys Pro Ala Pro Ile Gly Glu Phe Glu Lys Val Cys
            100                 105                 110

Ser Asn Asp Asn Lys Thr Phe Asp Ser Ser Cys His Phe Phe Ala Thr
        115                 120                 125

Lys Cys Thr Leu Glu Gly Thr Lys Lys Gly His Lys Leu His Leu Asp
    130                 135                 140

Tyr Ile Gly Pro Cys Lys Tyr Ile Pro Pro Cys Leu Asp Ser Glu Leu
145                 150                 155                 160

Thr Glu Phe Pro Leu Arg Met Arg Asp Trp Leu Lys Asn Val Leu Val
                165                 170                 175

Thr Leu Tyr Glu Arg Asp Glu Asp Asn Asn Leu Leu Thr Glu Lys Gln
            180                 185                 190

Lys Leu Arg Val Lys Lys Ile His Glu Asn Glu Lys Arg Leu Glu Ala
        195                 200                 205

Gly Asp His Pro Val Glu Leu Leu Ala Arg Asp Phe Glu Lys Asn Tyr
    210                 215                 220

Asn Met Tyr Ile Phe Pro Val His Trp Gln Phe Gly Gln Leu Asp Gln
225                 230                 235                 240

His Pro Ile Asp Gly Tyr Leu Ser His Thr Glu Leu Ala Pro Leu Arg
                245                 250                 255

Ala Pro Leu Ile Pro Met Glu His Cys Thr Thr Arg Phe Phe Glu Thr
            260                 265                 270
```

Cys Asp Leu Asp Asn Asp Lys Tyr Ile Ala Leu Asp Glu Trp Ala Gly
            275                 280                 285

Cys Phe Gly Ile Lys Gln Lys Asp Ile Asp Lys Asp Leu Val Ile
            290                 295                 300

<210> SEQ ID NO 4
<211> LENGTH: 3178
<212> TYPE: DNA
<213> ORGANISM: homo sapien

<400> SEQUENCE: 4

| | | | | | |
|---|---|---|---|---|---|
| gttgcctgtc | tctaaacccc | tccacattcc | cgcggtcctt | cagactgccc | ggagagcgcg | 60 |
| ctctgcctgc | cgcctgcctg | cctgccactg | agggttccca | gcaccatgag | ggcctggatc | 120 |
| ttctttctcc | tttgcctggc | cgggagggcc | ttggcagccc | ctcagcaaga | agccctgcct | 180 |
| gatgagacag | aggtggtgga | agaaactgtg | gcagaggtga | ctgaggtatc | tgtgggagct | 240 |
| aatcctgtcc | aggtggaagt | aggagaattt | gatgatggtg | cagaggaaac | cgaagaggag | 300 |
| gtggtggcgg | aaaatccctg | ccagaaccac | cactgcaaac | acggcaaggt | gtgcgagctg | 360 |
| gatgagaaca | cacccccat | gtgcgtgtgc | caggacccca | ccagctgccc | agcccccatt | 420 |
| ggcgagtttg | agaaggtgtg | cagcaatgac | aacaagacct | cgactcttc | ctgccacttc | 480 |
| tttgccacaa | agtgcaccct | ggagggcacc | aagaagggcc | acaagctcca | cctggactac | 540 |
| atcgggcctt | gcaaatacat | ccccccttgc | ctggactctg | agctgaccga | attccccctg | 600 |
| cgcatgcggg | actggctcaa | gaacgtcctg | gtcaccctgt | atgagaggga | tgaggacaac | 660 |
| aaccttctga | ctgagaagca | gaagctgcgg | gtgaagaaga | tccatgagaa | tgagaagcgc | 720 |
| ctggaggcag | agaccacccc | cgtggagctg | ctggcccggg | acttcgagaa | gaactataac | 780 |
| atgtacatct | tccctgtaca | ctggcagttc | ggccagctgg | accagcaccc | cattgacggg | 840 |
| tacctctccc | cacaccgagct | ggctccactg | cgtgctcccc | tcatccccat | ggagcattgc | 900 |
| accacccgct | ttttcgagac | ctgtgacctg | gacaatgaca | agtacatcgc | cctggatgag | 960 |
| tgggccggct | gcttcggcat | caagcagaag | gatatcgaca | aggatcttgt | gatctaaatc | 1020 |
| cactccttcc | acagtaccgg | attctctctt | taaccctccc | cttcgtgttt | ccccaatgt | 1080 |
| ttaaaatgtt | tggatggttt | gttgttctgc | ctggagacaa | ggtgctaaca | tagatttaag | 1140 |
| tgaatacatt | aacggtgcta | aaaatgaaaa | ttctaaccca | agacatgaca | ttcttagctg | 1200 |
| taacttaact | attaaggcct | tttccacacg | cattaatagt | cccattttc | tcttgccatt | 1260 |
| tgtagctttg | cccattgtct | tattggcaca | tgggtggaca | cggatctgct | gggctctgcc | 1320 |
| ttaaacacac | attgcagctt | caacttttct | ctttagtgtt | ctgtttgaaa | ctaatactta | 1380 |
| ccgagtcaga | ctttgtgttc | atttcatttc | agggtcttgg | ctgcctgtgg | gcttccccag | 1440 |
| gtggcctgga | ggtgggcaaa | gggaagtaac | agacacacga | tgttgtcaag | gatggttttg | 1500 |
| ggactagagg | ctcagtggtg | ggagagatcc | ctgcagaacc | caccaaccag | aacgtggttt | 1560 |
| gcctgaggct | gtaactgaga | gaaagattct | ggggctgtgt | tatgaaaata | tagacattct | 1620 |
| cacataagcc | cagttcatca | ccatttcctc | ctttaccttt | cagtgcagtt | tcttttcaca | 1680 |
| ttaggctgtt | ggttcaaact | tttgggagca | cggactgtca | gttctctggg | aagtggtcag | 1740 |
| cgcatcctgc | agggcttctc | ctcctctgtc | ttttggagaa | ccagggctct | tctcaggggc | 1800 |
| tctagggact | gccaggctgt | tcagccagg | aaggccaaaa | tcaagagtga | gatgtagaaa | 1860 |
| gttgtaaaat | agaaaaagtg | gagttggtga | atcggttgtt | ctttcctcac | atttggatga | 1920 |

```
ttgtcataag gttttagca tgttcctcct tttcttcacc ctccccttt ttcttctatt    1980 aatcaagaga aacttcaaag ttaatgggat ggtcggatct cacaggctga gaactcgttc    2040
acctccaagc atttcatgaa aaagctgctt cttattaatc atacaaactc tcaccatgat    2100
gtgaagagtt tcacaaatcc ttcaaaataa aagtaatga cttagaaact gccttcctgg    2160
gtgatttgca tgtgtcttag tcttagtcac cttattatcc tgacacaaaa acacatgagc    2220
atacatgtct acacatgact acacaaatgc aaacctttgc aaacacatta tgcttttgca    2280
cacacacacc tgtacacaca caccggcatg tttatacaca gggagtgtat ggttcctgta    2340
agcactaagt tagctgtttt catttaatga cctgtggttt aacccttttg atcactacca    2400
ccattatcag caccagactg agcagctata tcctttatt aatcatggtc attcattcat    2460
tcattcattc acaaaatatt tatgatgtat ttactctgca ccaggtccca tgccaagcac    2520
tggggacaca gttatggcaa agtagacaaa gcatttgttc atttggagct tagagtccag    2580
gaggaataca ttagataatg acacaatcaa atataaattg caagatgtca caggtgtgat    2640
gaagggagag taggagagac catgagtatg tgtaacagga ggacacagca ttattctagt    2700
gctgtactgt tccgtacggc agccactacc cacatgtaac tttttaagat ttaaatttaa    2760
attagttaac attcaaaacg cagctcccca atcacactag caacatttca agtgcttgag    2820
agccatgcat gattagtggt taccctattg aataggtcag aagtagaatc ttttcatcat    2880
cacagaaagt tctattggac agtgctcttc tagatcatca taagactaca gagcactttt    2940
caaagctcat gcatgttcat catgttagtg tcgtattttg agctggggtt ttgagactcc    3000
ccttagagat agagaaacag acccaagaaa tgtgctcaat tgcaatgggc cacataccta    3060
gatctccaga tgtcatttcc cctctcttat tttaagttat gttaagatta ctaaaacaat    3120
aaaagctcct aaaaaatcaa aaaaaaaaaa aaaaaaaaa aaaaaaaaaa aaaaaaa       3178
```

<210> SEQ ID NO 5
<211> LENGTH: 650
<212> TYPE: PRT
<213> ORGANISM: mus musculus

<400> SEQUENCE: 5

```
Met Lys Ala Val Leu Leu Leu Cys Ala Leu Gly Thr Ala Val Ala
1               5                   10                  15

Ile Pro Thr Ser Thr Arg Phe Leu Ser Asp His Ser Asn Pro Thr Thr
            20                  25                  30

Ala Thr Leu Val Thr Pro Glu Asp Ala Thr Val Pro Ile Ala Gly Val
        35                  40                  45

Glu Ala Thr Ala Asp Ile Glu Asn His Pro Asn Asp Lys Ala Glu Lys
    50                  55                  60

Pro Ser Ala Leu Asn Ser Glu Glu Glu Thr His Glu Gln Ser Thr Glu
65                  70                  75                  80

Gln Asp Lys Thr Tyr Ser Phe Glu Val Asp Leu Lys Asp Glu Glu Asp
                85                  90                  95

Gly Asp Gly Asp Leu Ser Val Asp Pro Thr Glu Gly Thr Leu Thr Leu
            100                 105                 110

Asp Leu Gln Glu Gly Thr Ser Glu Pro Gln Gln Lys Ser Leu Pro Glu
        115                 120                 125

Asn Gly Asp Phe Pro Ala Thr Val Ser Thr Ser Tyr Val Asp Pro Asn
    130                 135                 140

Gln Arg Ala Asn Ile Thr Lys Gly Lys Glu Ser Gln Glu Gln Pro Val
145                 150                 155                 160
```

```
Ser Asp Ser His Gln Gln Pro Asn Glu Ser Ser Lys Gln Thr Gln Asp
                165                 170                 175

Leu Lys Ala Glu Glu Ser Gln Thr Gln Asp Pro Asp Ile Pro Asn Glu
            180                 185                 190

Glu Glu Glu Glu Glu Glu Asp Glu Glu Glu Glu Glu Glu Glu Glu Pro
        195                 200                 205

Glu Asp Ile Gly Ala Pro Ser Asp Asn Gln Glu Glu Gly Lys Glu Pro
    210                 215                 220

Leu Glu Glu Gln Pro Thr Ser Lys Trp Glu Gly Asn Arg Glu Gln Ser
225                 230                 235                 240

Asp Asp Thr Leu Glu Glu Ser Ser Gln Pro Thr Gln Ile Ser Lys Thr
                245                 250                 255

Glu Lys His Gln Ser Glu Gln Gly Asn Gln Gly Gln Glu Ser Asp Ser
            260                 265                 270

Glu Ala Glu Gly Glu Asp Lys Ala Ala Gly Ser Lys Glu His Ile Pro
        275                 280                 285

His Thr Glu Gln Gln Asp Gln Glu Gly Lys Ala Gly Leu Glu Ala Ile
    290                 295                 300

Gly Asn Gln Lys Asp Thr Asp Glu Lys Ala Val Ser Thr Glu Pro Thr
305                 310                 315                 320

Asp Ala Ala Val Val Pro Arg Ser His Gly Ala Gly Asp Asn Gly
                325                 330                 335

Gly Gly Asp Asp Ser Lys His Gly Ala Gly Asp Asp Tyr Phe Ile Pro
            340                 345                 350

Ser Gln Glu Phe Leu Glu Ala Glu Arg Met His Ser Leu Ser Tyr Tyr
        355                 360                 365

Leu Lys Tyr Gly Gly Gly Glu Glu Thr Thr Thr Gly Glu Ser Glu Asn
    370                 375                 380

Arg Arg Glu Ala Ala Asp Asn Gln Glu Ala Lys Lys Ala Glu Ser Ser
385                 390                 395                 400

Pro Asn Ala Glu Pro Ser Asp Glu Gly Asn Ser Arg Glu His Ser Ala
                405                 410                 415

Gly Ser Cys Thr Asn Phe Gln Cys Lys Arg Gly His Ile Cys Lys Thr
            420                 425                 430

Asp Pro Gln Gly Lys Pro His Cys Val Cys Gln Asp Pro Glu Thr Cys
        435                 440                 445

Pro Pro Ala Lys Ile Leu Asp Gln Ala Cys Gly Thr Asp Asn Gln Thr
    450                 455                 460

Tyr Ala Ser Ser Cys His Leu Phe Ala Thr Lys Cys Arg Leu Glu Gly
465                 470                 475                 480

Thr Lys Lys Gly His Gln Leu Gln Leu Asp Tyr Phe Gly Ala Cys Lys
                485                 490                 495

Ser Ile Pro Ala Cys Thr Asp Phe Glu Val Ala Gln Phe Pro Leu Arg
            500                 505                 510

Met Arg Asp Trp Leu Lys Asn Ile Leu Met Gln Leu Tyr Glu Pro Asn
        515                 520                 525

Pro Lys His Gly Gly Tyr Leu Asn Glu Lys Gln Arg Ser Lys Val Lys
    530                 535                 540

Lys Ile Tyr Leu Asp Glu Lys Arg Leu Leu Ala Gly Asp His Pro Ile
545                 550                 555                 560

Glu Leu Leu Leu Arg Asp Phe Lys Lys Asn Tyr His Met Tyr Val Tyr
                565                 570                 575
```

-continued

```
Pro Val His Trp Gln Phe Asn Glu Leu Asp Gln His Pro Ala Asp Arg
            580                 585             590

Ile Leu Thr His Ser Glu Leu Ala Pro Leu Arg Ala Ser Leu Val Pro
            595                 600             605

Met Glu His Cys Ile Thr Arg Phe Phe Glu Glu Cys Asp Pro Asn Lys
        610                 615             620

Asp Lys His Ile Thr Leu Lys Glu Trp Gly His Cys Phe Gly Ile Lys
625                 630                 635                 640

Glu Glu Asp Ile Asp Glu Asn Leu Leu Phe
                645             650
```

MODULATION OF SYNAPTOGENESIS

FEDERALLY-SPONSORED RESEARCH OR DEVELOPMENT

This invention was made with Government support under contracts NS045621 and DA015043 awarded by the National Institutes of Health. The Government has certain rights in this invention.

BACKGROUND OF THE INVENTION

Synapses are specialized cell adhesions that are the fundamental functional units of the nervous system, and they are generated during development with amazing precision and fidelity. During synaptogenesis, synapses form, mature, and stabilize and are also eliminated by a process that requires intimate communication between pre- and postsynaptic partners. In addition, there may be environmental determinants that help to control the timing, location, and number of synapses.

Synapses occur between neuron and neuron and, in the periphery, between neuron and effector cell, e.g. muscle. Functional contact between two neurons may occur between axon and cell body, axon and dendrite, cell body and cell body, or dendrite and dendrite. It is this functional contact that allows neurotransmission. Many neurologic and psychiatric diseases are caused by pathologic overactivity or underactivity of neurotransmission; and many drugs can modify neurotransmission, for examples hallucinogens and antipsychotic drugs.

During recent years, a great deal of effort has been made by investigators to characterize the function of synaptic proteins, which include synaptotagmin, syntexin, synaptophysin, synaptobrevin, and the synapsins. These proteins are involved in specific aspects of synaptic function, e.g. synaptic vesicle recycling or docking, and in the organization of axonogenesis, differentiation of presynaptic terminals, and in the formation and maintenance of synaptic connections.

Only by establishing synaptic connections can nerve cells organize into networks and acquire information processing capability such as learning and memory. Synapses are progressively reduced in number during normal aging, and are severely disrupted during neurodegenerative diseases. Therefore, finding molecules capable of creating and/or maintaining synaptic connections is an important step in the treatment of neurodegenerative diseases.

Astrocytes are the most abundant cell type in the brain, which ensheathe synapses throughout the central nervous system (CNS). They have been traditionally viewed as synaptic support cells, clearing ions and neurotransmitters from the synaptic cleft. Accumulating evidence has shown that astrocytes play an active role in the formation and function of synapses (see, for example, Ullian et al. (2004) Glia 47(3): 209-16; Ullian et al. (2004). Mol Cell Neurosci 25(2): 241-51; Christopherson et al. (2005). Cell 120(3): 421-33; Elmariah et al. (2005). J Neurosci 25(14): 3638-50).

It has been particularly difficult to study the role of glia in synaptogenesis in vitro because most CNS neuronal cultures contain glia, which are crucial for neuronal survival. For example, see culture conditions in Meyer-Franke et al. (1995) Neuron 15(4): 805-19. The modulation of synapse formation is of great interest for the treatment of a variety of nervous system disorders. To date, few soluble molecules have been identified that are sufficient to induce or increase the number of CNS synapses. Also of interest are soluble molecules capable of negatively modulating the formation of CNS synapses.

SUMMARY OF THE INVENTION

Methods are provided for the modulation of synaptogenesis with soluble factors. It has been found that contacting neuronal cells with the soluble polypeptide Hevin is sufficient to increase synapse formation on the neuronal cells. It has further been found that the soluble polypeptide SPARC specifically antagonizes the synaptogenic activity of Hevin. Hevin, or agonists and mimetics thereof, are utilized to enhance synaptogenesis. Hevin inhibitors or antagonists, such as SPARC, are utilized to decrease or block synaptogenesis.

In one embodiment of the invention, methods are provided for screening candidate agents for the ability to modulate synapse formation. In one embodiment of the invention the neurons are neurons in the central nervous system. In another embodiment, the neurons are peripheral nervous system neurons. Screening may be performed in vitro or in vivo.

Methods are provided for protecting or treating an individual suffering from adverse effects of deficits in synaptogenesis, or from undesirably active synaptogenesis. These findings have broad implications for a variety of clinical conditions, including traumatic brain injury, epilepsy, and other conditions where synapses fail to form or form inappropriately. Synaptogenesis is enhanced by contacting neurons with agents that are specific agonists or analogs of Hevin. Conversely, synaptogenesis is inhibited by contacting neurons with inhibitors or antagonists of Hevin such as SPARC and SPARC agonists and analogs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2E: Hevin induces an increase in the number of co-localized pre and postsynaptic puncta in RGCs. Immunostaining of RGCs for colocalization of presynaptic Bassoon (red) and postsynaptic Homer (green) showed few co-localized synaptic puncta in the absence of astrocytes (A) but many in the presence a feeding layer of astrocytes (B) or 20 nM of TSP (C) or 30 nM recombinant Hevin (D). (E) Quantification of the effects of Astrocytes, Hevin and TSP on synaptic puncta. Astrocytes, TSP and Hevin all significantly increased the number of co-localized synaptic puncta over RGCs alone ($*p<0.05$, n=20, error bars indicate SEM values).

Hevin increased the number of synapses formed by RGCs 5-7 fold similar to the effect of astrocytes. (* $p<0.05$) (C, D) Astrocytes, TSP and Hevin increased the total number of synaptic vesicles released. Presynaptic sites were labeled with FM4-64 FX in high K+ (D, depolarization) or over a period of 15 minutes in physiological external buffer (E, spontaneous). In RGCs cultured in the absence of astrocytes fewer sites were labeled with FM4-64 FX. Conversely, RGCs cultured with astrocytes, TSP or Hevin, FM4-64FX labeled puncta were 5 fold more (* $p<0.05$, n=20, error bars indicate SEM values). (E) Representative traces from whole cell patch clamp recordings of RGCs cultured with astrocytes, alone, with 30 nM Hevin or with 20 μM TSP. Only the RGCs cultured with astrocytes had postsynaptic events.

FIGS. 4A-4G: SPARC antagonizes Hevin's synaptogenic activity. (A) Hevin was immunodepleted from mouse ACM with a rabbit polyclonal antibody against mouse Hevin bound to Protein A/G beads (Pierce). The ACM was incubated with the antibody bound beads for 3 hours and this procedure was repeated for 3 rounds. Hevin was detected by a Rat monoclonal antibody against mouse Hevin (12:155) by western blotting. Rectangle indicates 130 kDa molecular weight marker. After the 3rd round of depletion, no Hevin was detected in the ACM. Mock depletion was performed in parallel with Protein A/G beads without any antibody. Hevin is preserved after mock depletion. (B) RGCs cultured with Hevin-depleted ACM form fewer synapses compared to RGCs treated with Mock-depleted ACM though there are still many co-localized pre and post synaptic puncta. Hevin depletion also led to a decrease in the synaptic puncta size and general presynaptic Synaptotagmin clustering (see inlays). (C) Number of synapses formed by Hevin depleted ACM was 40% less that the number of synapses formed by mock-depleted ACM (top). There was a significant decrease in the size of synaptic puncta in the absence of Hevin (bottom). (D) SPARC (100 nM) did not increase the number of synapses formed by RGCs, but there was an increase in the number of PSD-95 puncta (inlay). (E) While Hevin induced formation of synapses. (F) Interestingly addition of Hevin (30 nM) and SPARC (100 nM) together led to the complete loss of Hevin's synaptogenic activity, although pre and post synaptic clusters were still visible (inlay). In addition presynaptic puncta were excluded from the cell body and proximal dendrites. (G) Quantification of the co-localized synaptic puncta number per cell for RGCs cultured alone, with astrocytes, Hevin (30 nM), SPARC (100 nM), Hevin plus SPARC, TSP (20 nM) or TSP+SPARC. Astrocytes, Hevin or TSP induced a significant increase in synapse number when compared to RGCs cultured alone. SPARC antagonized Hevin's synaptogenic effect but not that of TSP ($p<0.05$, n=20, error bars indicate SEM values).

Figure 5:
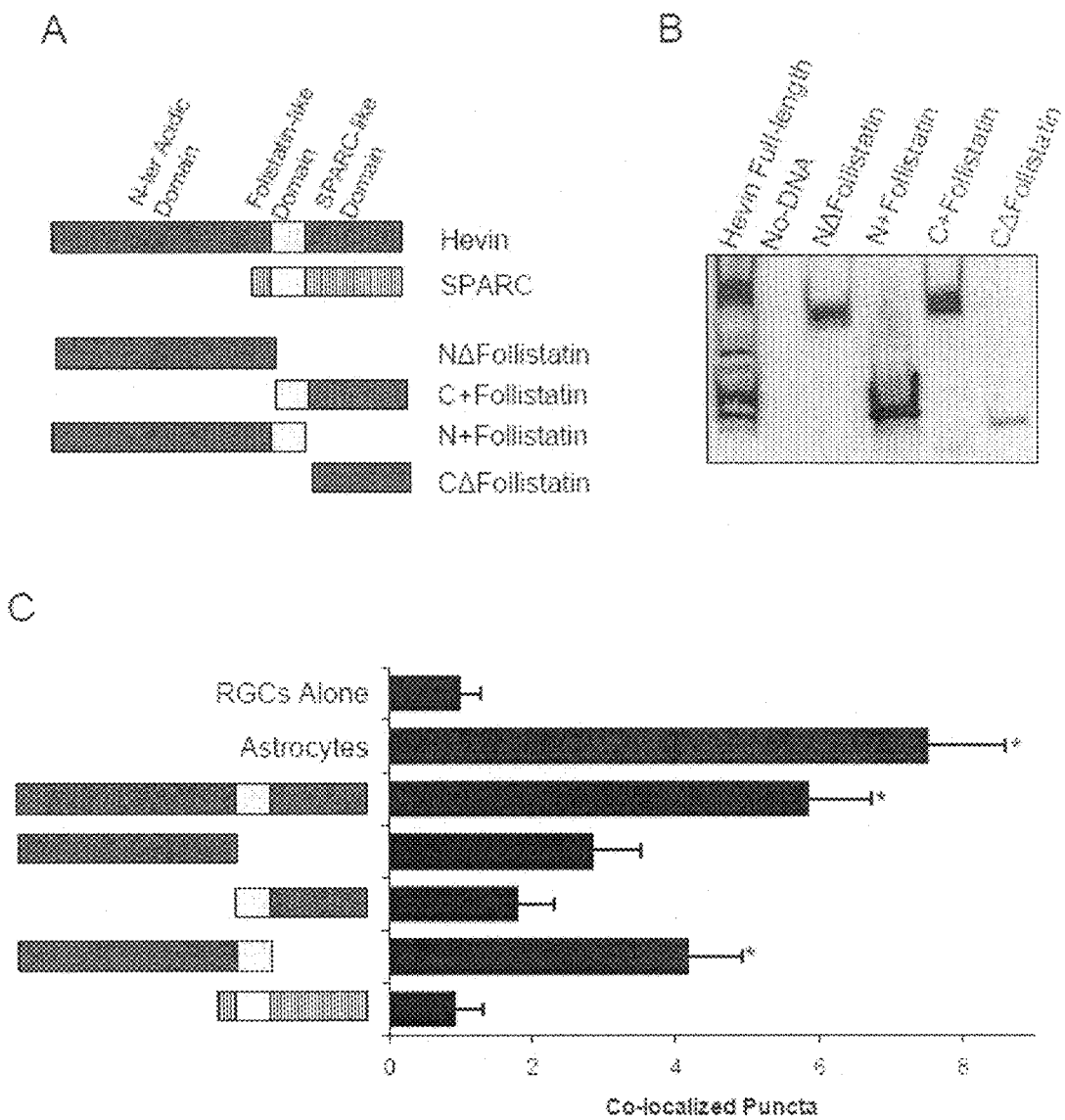

FIGS. 5A-5C: Hevin's synaptogenic function is mapped to its N-terminal acidic domain plus follistatin-like repeat. (A) Schematic presentation of domain structure of Hevin, Hevin truncation constructs and SPARC. (B) Expression constructs for full length Hevin, NΔFollistatin, N+Follistatin, C+Follistatin and CΔFollistatin constructs were transfected into HEK293 cells. Cell conditioned media from each transfection was run on a 4-15% SDSPAGE gel and proteins were transferred to a PVDF membrane. The recombinant Hevin and Hevin truncation constructs were then detected by a mouse monoclonal against Histidine tag (Qiagen). (C) Quantification of the co-localized synaptic puncta number per cell for RGCs cultured alone, with astrocytes, Hevin and Hevin truncation constructs (30 nM) or SPARC (30 nM). N+Follistatin construct increased synapse number significantly when compared to RGCs alone condition ($p<0.05$, n=20, error bars indicate SEM values).

Figure 6:
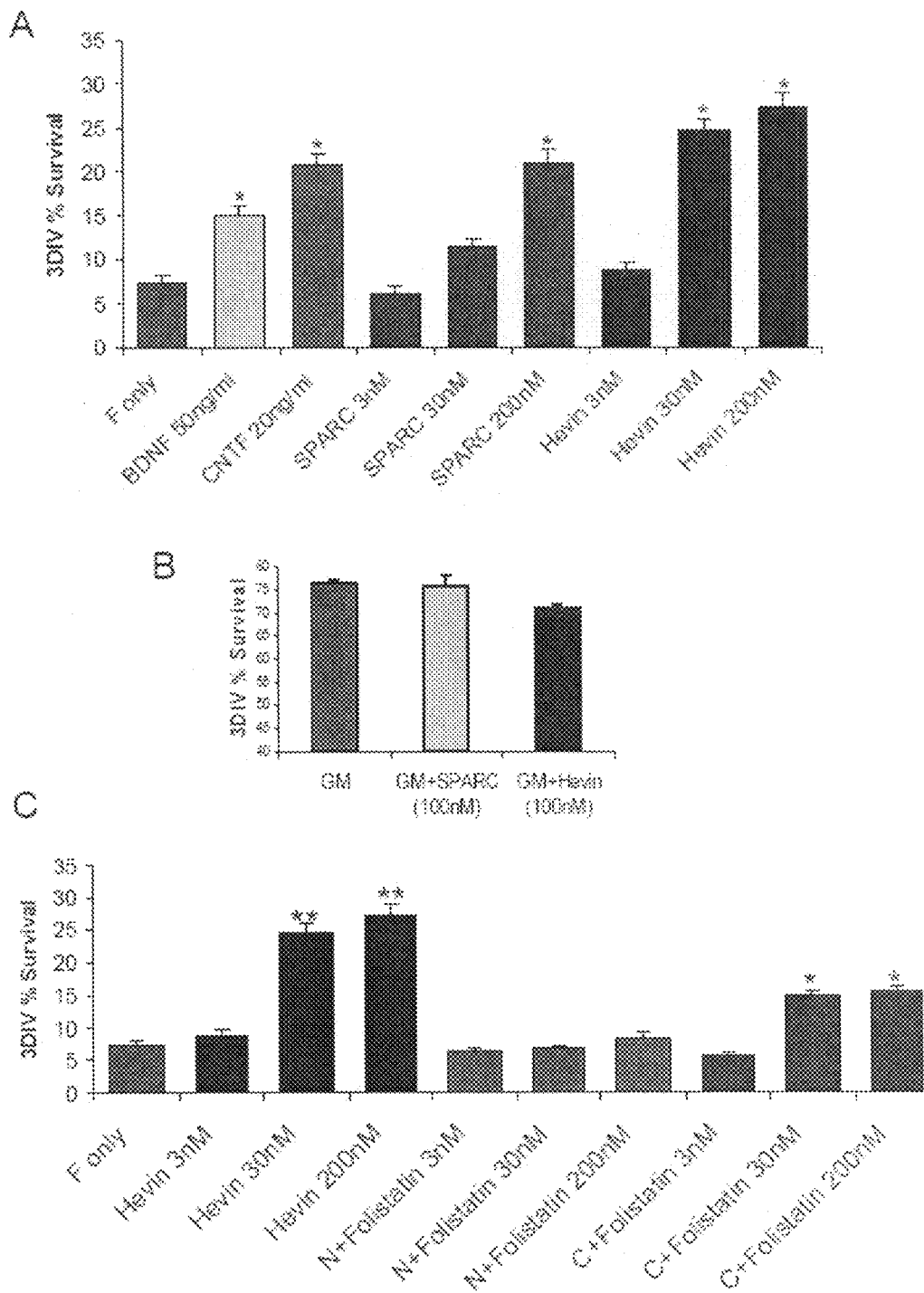

FIGS. 6A-6C: Hevin promotes RGC survival but this activity maps to a different domain than its synaptogenic effect. (A) Hevin and SPARC promoted 3DIV RGC survival in minimal media containing Forskolin similar to the neurotrophic factors BDNF and CNTF. (B) Hevin or SPARC did not provide additional survival effect when added to RGC growth media (GM) which contains B27, Insulin, CNTF and BDNF. (C) Hevin's survival promoting activity is in its C-terminal domain. (* $p<0.05$, ** $p<0.001$)

FIG. 7: Hevin promotes neurite outgrowth and branching in RGCs. Clonal density RGCs were cultured for 24 hours alone or with 30 nM Hevin, N+Follistatin, C+Follistatin, SPARC or 100 nM SPARC. The cells were then fixed and stained with beta-tubulin (TuJ1 antibody, Sigma). Cell bodies and neurites were imaged (n>300) for each condition and the images were analyzed by Metamorph Software. The total outgrowth/cell (A) and branches/cell values were calculated (*$p<0.05$, ** $p<0.001$).

FIGS. 8A-8B: Hevin and SPARC expression in vivo correlate with the synapse formation. (A) 12 μm sagital sections of postnatal day 5 (p5, upper panels) and p25 (lower panels) were stained with rat anti Hevin monoclonal antibody (12:155) and mouse anti SPARC monoclonal antibody (236). Anti-rat 594 and anti-mouse 488 fluorophore conjugated secondary antibodies were used to detect the staining. Superior colliculi were imaged. (B) Same staining was performed in the absence of Hevin and SPARC specific primary antibodies to detect only secondary antibody nonspecific staining.

DETAILED DESCRIPTION OF THE INVENTION

Methods are provided for modulating synaptogenesis. These findings have implications for a variety of clinical conditions, including traumatic brain injury, epilepsy, and other conditions where synapses fail to form or form inappropriately. Synaptogenesis is enhanced by contacting neurons with Hevin or agents that are specific agonists of Hevin. Conversely, synaptogenesis is inhibited by contacting neurons with inhibitors or antagonists of Hevin, including SPARC.

It is demonstrated herein that the soluble proteins Hevin; SPARC; and agonists and antagonists thereof can trigger or antagonize synapse formation. Such proteins are synthesized in vitro and in vivo by astrocytes.

Delivery of exogenous Hevin or an agonist thereof induces new synapses in normal neurons. The ability to restore synaptogenesis in an adult has important implications for enhancing memory in normal brain; for treatment of Alzheimer's disease (a disease where synapses are lost), as well as promoting new synaptogenesis in repair and regeneration of injured CNS after stroke or spinal cord injury; enhancement of neuromuscular junctions in muscular dystrophy; and the like. Delivery of exogenous Hevin or an agonist thereof also find use in combination with administration of neural progenitors, or increases in neurogenesis, in order to promote functional connections between the nascent neurons and other neurons and effector cells.

Hevin antagonists such as SPARC are useful in treating diseases of excess, unwanted synapses, for example after injury in which "reactive astrocytes", form glial scars (Mendis et al., Brain Res. (1996) Aug. 19; 730:1-2 pp. 95-106). Glial scars are associated with epileptic loci, and may induce the unwanted excess synaptogenesis that underlies epilepsy.

Similarly there are unwanted extra synapses that underlie the long-lived drug craving of addiction.

Definitions

Synapses are asymmetric communication junctions formed between two neurons, or, at the neuromuscular junction (NMJ) between a neuron and a muscle cell. At an archetypal chemical synapse, such as those found at dendritic spines, a mushroom-shaped bud projects from each of two cells and the caps of these buds press flat against one another. At this interface, the membranes of the two cells flank each other across a slender gap, the narrowness of which enables signaling molecules known as neurotransmitters to pass rapidly from one cell to the other by diffusion. This gap, which is about 20 nm wide, is known as the synaptic cleft.

Chemical synapses enable cell-to-cell communication via secretion of neurotransmitters, whereas in electrical synapses signals are transmitted through gap junctions, specialized intercellular channels that permit ionic current flow. In addition to ions, other molecules that modulate synaptic function (such as ATP and second messenger molecules) can diffuse through gap junctional pores. At the mature NMJ, pre- and postsynaptic membranes are separated by the synaptic cleft containing extracellular proteins that form the basal lamina. Synaptic vesicles are clustered at the presynaptic release site, transmitter receptors are clustered in junctional folds at the postsynaptic membrane, and glial processes surround the nerve terminal.

Synapses are asymmetric both in structure and in how they operate. Only the so-called presynaptic neuron secretes the neurotransmitter, which binds to receptors facing into the synapse from the postsynaptic cell. The pre-synaptic nerve terminal (also called the synaptic button or bouton) generally buds from the tip of an axon, while the post-synaptic target surface typically appears on a dendrite, a cell body, or another part of a cell. The parts of synapses where neurotransmitters are released are called the active zones. At active zones the membranes of the two adjacent cells are held in close contact by cell adhesion proteins. Immediately behind the postsynaptic membrane is an elaborate complex of interlinked proteins called the postsynaptic density. Proteins in the postsynaptic density serve a myriad of roles, from anchoring and trafficking neurotransmitter receptors into the plasma membrane, to anchoring various proteins which modulate the activity of the receptors. The postsynaptic cell need not be a neuron, and can also be gland or muscle cell.

The release of a neurotransmitter is triggered by the arrival of a nerve impulse (or action potential) and occurs through an unusually rapid process of cellular secretion known as exocytosis. Within the pre-synaptic nerve terminal, vesicles containing neurotransmitter are docked at the synaptic membrane. The arriving action potential produces an influx of calcium ions through voltage-dependent, calcium-selective ion channels. Calcium ions then trigger a biochemical cascade which results in vesicles fusing with the presynaptic-membrane and releasing their contents to the synaptic cleft. Vesicle fusion is driven by the action of a set of proteins in the presynaptic terminal known as SNAREs. The membrane added by this fusion is retrieved by endocytosis and recycled for the formation of fresh neurotransmitter-filled vesicles. Receptors on the opposite side of the synaptic gap bind neurotransmitter molecules and respond by opening nearby ion channels in the post-synaptic cell membrane, causing ions to rush in or out and changing the local transmembrane potential of the cell. The resulting change in voltage is called a postsynaptic potential, which can be measured by patch-clamping and other suitable techniques.

Synaptogenesis. Synaptogenesis, as used herein, refers to the process by which pre- and/or post-synapses form on a neuron. Enhancing synaptogenesis results in an increased number of synapses, while inhibiting synaptogenesis results in a decrease in the number of synapses, or a lack of increase where an increase would otherwise occur. By "augmentation" or "modulation" of synaptogenesis as used herein, it is meant that the number of synapses formed is either enhanced or suppressed as required in the specific situation. As used herein, the term "modulator of synaptogenesis" refers to an agent that is able to alter synapse formation. Modulators include, but are not limited to, both "activators" and "inhibitors". An "activator" or "agonist" is a substance that enhances synaptogenesis. Conversely, an "inhibitor" or "antagonist" decreases the number of synapses. The reduction may be complete or partial. As used herein, modulators encompass Hevin, SPARC, their analogs, antagonists and agonists.

Synaptogenesis is a dynamic process. During development, more synapses are established than ultimately will be retained. Therefore, the elimination of excess synaptic inputs is a critical step in synaptic circuit maturation. Synapse elimination is a competitive process that involves interactions between pre- and postsynaptic partners. In the CNS, as with the NMJ, a developmental, activity-dependent remodeling of synaptic circuits takes place by a process that may involve the selective stabilization of coactive inputs and the elimination of inputs with uncorrelated activity. The anatomical refinement of synaptic circuits occurs at the level of individual axons and dendrites by a dynamic process that involves rapid elimination of synapses. As axons branch and remodel, synapses form and dismantle with synapse elimination occurring rapidly.

Agonists and antagonists may include proteins, nucleic acids, carbohydrates, antibodies, or any other molecules that modulate the effect of a protein. The term analog is used herein to refer to a molecule that structurally resembles a molecule of interest but which has been modified or identified in a targeted and controlled manner, by replacing a specific substituent of the reference molecule with an alternate substituent. Compared to the starting molecule, an analog may exhibit the same, similar, or improved utility. Synthesis and screening of analogs, to identify variants of known compounds having improved traits (such as higher potency at a specific receptor type, or higher selectivity at a targeted receptor type and lower activity levels at other receptor types) is an approach that is well known in pharmaceutical chemistry. In the cases of Kevin and SPARC, some analogs contain one, two, or three domains characterized in the SPARC family of proteins, or peptides derived therefrom.

A number of cell adhesion molecules and tyrosine kinase receptor ligands have been implicated in modulating synaptogenesis. Integrins, cadherins, and neuroligins, are cell adhesion molecules that may play a role in synapse formation. The ephrins and their receptors, the Eph tyrosine kinases, participate in the activity-independent topographic organization of brain circuits and may also participate in synapse formation and maturation. Neurotrophins have also been implicated in aspects of synapse development and function.

Hevin and SPARC. As used herein, the term "Hevin" refers to the matricellular secreted glycoprotein in the secreted protein acidic and rich in cysteine (SPARC) family which is also known as SC1, MAST 9, SPARC-like 1, and ECM 2. The human polypeptide sequence is provided as SEQ ID NO:1, and the genetic sequence as SEQ ID NO:2 (see Girard and Springer (1995) Immunity 2 (1), 113-123). For reference purposes, the mouse protein is provided herein as SEQ ID NO:5. Hevin is the product of a single-copy gene that has been mapped to mouse chromosome 5 and to human chromosome 4q 22-25, a region deleted in many human cancers (Isler et al., 2001). Its genomic organization is similar in mouse and human, with 11 exons and 10 introns that span ~35 kb in mouse and ~47 kb in human. An mRNA of ~3 kb is characteristically transcribed from the hevin gene. Human hevin is a protein of ~650 amino acids and an encoded molecular weight of 71 kDa that is post-translationally modified by N-linked glycosylation. Hevin has the Genbank accession number NM_004684. It is a multidomain protein that associates with the extracellular matrix and posSesses a variety of biologic functions.

SPARC may be accessed at Genbank, NM_003118.2, as described by Young et al. (1990) Connect. Tissue Res. 24 (1), 17-28. The human polypeptide sequence is provided as SEQ ID NO:3, and the genetic sequence as SEQ ID NO:4.

Hevin contains three major domains, based on primary sequence alignment with SPARC, which is herein disclosed to be a specific antagonist of the synaptogenic activity of Hevin. The characterization of SPARC has revealed the following information about its signature domains.

The N-terminal acidic domain (pK<4) is the least conserved domain within the SPARC family. It is highly sensitive to interaction with Ca2+, which stabilizes the predicted α-helical regions (see Brekken and Sage (2001) Matrix Biol. 19(8):816-27 and Bradshaw and Sage (2001) J Clin Invest. 107(9):1049-54, each herein specifically incorporated by reference with respect to teachings of SPARC and hevin domain structure). The N-terminal domain binds five to eight Ca2+ ions with Kd of $10^{-3}$ to $10^{-5}$ M, contains immunodominant epitopes, and binds to hydroxyapatite. In addition, synthetic peptides from this region have been shown to inhibit endothelial cell spreading, chemotaxis to fibroblast growth factor (FGF-2), and the production of fibronectin and thrombospondin 1 (TSP).

The follistatin-like (FS) domain shares 56% identity with SPARC, and is homologous to a repeated domain in follistatin, a protein that inhibits several members of the TGF-β superfamily. Residues 440-495 of the module, of mixed α/β structure, resemble a serine protease inhibitor of the Kazal family, whereas the N-terminus of the module is a β-hairpin similar to that of epidermal growth factor. The FS domain contains most of the cysteine residues of the protein, all of which are disulfide-bonded, as well as two high-affinity $Cu^{2+}$-binding regions and an N-linked complex carbohydrate. The $Cu^{2+}$-binding regions, in particular, have been shown to regulate endothelial cell proliferation and angiogenesis; other peptides from this domain abrogate focal adhesions and inhibit the cell cycle.

The extracellular $Ca^{2+}$-binding (EC) domain is highly conserved and unique within the SPARC family, with hevin and SPARC sharing 61% identity. It consists of a characteristic amphipathic α-helix as well as two EF-hand motifs, one canonical and one variant. In addition, the EC domain has been shown to interact with the FS domain via several conserved residues to stabilize $Ca^{2+}$ binding. Peptides from EF-hand 2 in this domain have been shown to bind to cells, to inhibit cell spreading and proliferation, and to reverse focal adhesion formation.

Certain constructs are utilized herein that utilize specific functional domains of Hevin. The domains are illustrated in the mouse protein, but one of skill in the art will readily understand that the mouse and human proteins can be aligned and the corresponding regions of the human protein determined. For example, among the constructs depicted in FIG. 5, the full-length "hevin" construct comprises an Ig κ-chain secretion signal peptide; and N-terminal myc and his tags, in addition to the full length Hevin sequence. The NterΔfollistatin construct has a deletion of the signal sequence (SEQ ID NO:5, residues 1-16) and the follistastin domain plus C terminus (SEQ ID NO:5, residues 418-650; which corresponds to a deletion in SEQ ID NO:1, residues 432-664). The C+Follistatin construct has a deletion of residues 1-416 of SEQ ID NO:5; which corresponds to a deletion of residues 1-432 in SEQ ID NO:1. The N+Follistatin construct has a deletion of the signal sequence (SEQ ID NO:5, residues 1-16); and the C terminus (SEQ ID NO:5, residues 459-650; which corresponds to a deletion in SEQ ID NO:1, residues 477-664). The CΔFollistatin construct has a deletion of SEQ ID NO:5, residues 1-458; which corresponds to a deletion in SEQ ID NO:1 of residues 1-477.

For use in the subject methods, any native Hevin or SPARC form, modifications thereof, or a combination of forms may be used. Peptides of interest include fragments of at least about 12 contiguous amino acids, more usually at least about 20 contiguous amino acids, and may comprise 30 or more amino acids, up to a complete domain, or the complete polypeptide. Preferred polypeptides include the N-terminal acidic domain; and may further include the Follistatin-like domain.

The sequence of a Hevin or SPARC polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) J. Biol. Chem. 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Conditions of Interest

By "neurological" or "cognitive" function as used herein, it is meant that the increase of synapses in the brain enhances the patient's ability to think, function, etc. In conditions where there is axon loss and regrowth, there may be recovery of motor and sensory abilities. As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

Among the conditions of interest for the present methods of enhancing synaptogenesis are senescence, stroke, spinal cord injury, Alzheimer's disease (a disease where synapses are lost), as well as promoting new synaptogenesis in repair and regeneration of injured CNS after stroke or spinal cord injury. Such conditions benefit from administration of Hevin or Hevin agonists, which increase, or enhance, the development of synapses. In some instances, where there has been neuronal loss, it may be desirable to enhance neurogenesis as well, e.g. through administration of agents or regimens that increase neurogenesis, transplantation of neuronal progenitors, etc.

The glaucomas are a group of eye disorders characterized by progressive optic nerve damage at least partly due to increased intraocular pressure (IOP). Glaucoma is the 2nd most common cause of blindness. There is massive synapse loss onto retinal ganglion cells, accompanied by cell death. Hevin is a profoundly strong neurotrophic factor for retinal ganglion cells, equal in activity to the other two known strong neurotrophic factors for retinal ganglion cells (which are brain derived neurotrophic factor (BDNF) and ciliary neurotrophic factor (CNTF)), but in addition also induces synaptogenesis (which BDNF and CNTF do not). Hevin may be administered to glaucoma patients topically or systemically, e.g. by direct administration to the retinal ganglion cells in affected individuals.

Axons of retinal ganglion cells travel through the optic nerve carrying images from the eye to the brain. Damage to these axons causes ganglion cell death with resultant optic nerve atrophy and patchy visual loss. Elevated IOP (normal range, 11 to 21 mm Hg) plays a role in axonal damage, either by direct nerve compression or diminution of blood flow. However, the relationship between pressure and nerve damage is variable.

Symptoms and signs vary with type of glaucoma, but the defining characteristic is optic nerve damage as evidenced by an abnormal optic disk and certain types of visual field deficits. Visual deficits of the optic nerve include nasal step defects (which do not cross the horizontal meridian), arcuate scotomata extending nasally from the blind spot, temporal wedge defects, and paracentral scotomata. Deficits of the more proximal visual pathways (ie, from the lateral geniculate nucleus to the occipital lobe) involve quadrants or hemispheres of the visual field. IOP may be elevated or within the average range.

The term "stroke" broadly refers to the development of neurological deficits associated with impaired blood flow to the brain regardless of cause. Potential causes include, but are not limited to, thrombosis, hemorrhage and embolism. Current methods for diagnosing stroke include symptom evaluation, medical history, chest X-ray, ECG (electrical heart activity), EEG (brain nerve cell activity), CAT scan to assess brain damage and MRI to obtain internal body visuals. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from a tumor, or other blood loss.

By "ischemic episode" is meant any circumstance that results in a deficient supply of blood to a tissue. When the ischemia is associated with a stroke, it can be either global or focal ischemia, as defined below. The term "ischemic stroke" refers more specifically to a type of stroke that is of limited extent and caused due to blockage of blood flow. Cerebral ischemic episodes result from a deficiency in the blood supply to the brain. The spinal cord, which is also a part of the central nervous system, is equally susceptible to ischemia resulting from diminished blood flow.

By "focal ischemia," as used herein in reference to the central nervous system, is meant the condition that results from the blockage of a single artery that supplies blood to the brain or spinal cord, resulting in damage to the cells in the territory supplied by that artery.

By "global ischemia," as used herein in reference to the central nervous system, is meant the condition that results from a general diminution of blood flow to the entire brain, forebrain, or spinal cord, which causes the death of neurons in selectively vulnerable regions throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension.

Stroke can be modeled in animals, such as the rat (for a review see Duverger et al. (1988) *J Cereb Blood Flow Metab* 8(4):449-61), by occluding certain cerebral arteries that prevent blood from flowing into particular regions of the brain, then releasing the occlusion and permitting blood to flow back into that region of the brain (reperfusion). These focal ischemia models are in contrast to global ischemia models where blood flow to the entire brain is blocked for a period of time prior to reperfusion. Certain regions of the brain are particularly sensitive to this type of ischemic insult. The precise region of the brain that is directly affected is dictated by the location of the blockage and duration of ischemia prior to reperfusion. One model for focal cerebral ischemia uses middle cerebral artery occlusion (MCAO) in rats. Studies in normotensive rats can produce a standardized and repeatable infarction. MCAO in the rat mimics the increase in plasma catecholamines, electrocardiographic changes, sympathetic nerve discharge, and myocytolysis seen in the human patient population.

The methods of the invention are also useful for treatment of injuries to the central nervous system that are caused by mechanical forces, such as a blow to the head or spine, and which, in the absence of treatment, result in neuronal death, or severing of axons. Trauma can involve a tissue insult such as an abrasion, incision, contusion, puncture, compression, etc., such as can arise from traumatic contact of a foreign object with any locus of or appurtenant to the head, neck, or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracranial hematoma or edema). Similarly, traumatic constriction or compression can arise from the presence of a mass of abnormal tissue, such as a metastatic or primary tumor.

Senescence refers to the effects or the characteristics of increasing age, particularly with respect to the diminished ability of somatic tissues to regenerate in response to damage, disease, and normal use. Alternatively, aging may be defined in terms of general physiological characteristics. The rate of aging is very species specific, where a human may be aged at about 50 years; and a rodent at about 2 years. In general terms, a natural progressive decline in body systems starts in early adulthood, but it becomes most evident several decades later. One arbitrary way to define old age more precisely in humans is to say that it begins at conventional retirement age, around about 60, around about 65 years of age. Another definition sets parameters for aging coincident with the loss of reproductive ability, which is around about age 45, more usually around about 50 in humans, but will, however, vary with the individual. Loss of synaptic function may be found in aged individuals.

Among the aged, Alzheimer's disease is a serious condition. Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons >60 yr old, and its incidence increases as age advances. It accounts for more than 65% of the dementias in the elderly.

The essential features of dementia are impairment of short-term memory and long-term memory, abstract thinking, and judgment; other disturbances of higher cortical function; and personality change. Progression of cognitive impairment confirms the diagnosis, and patients with Alzheimer's disease do not improve.

The methods of the invention find also find use in combination with cell or tissue transplantation to the central nervous system, where such grafts include neural progenitors such as those found in fetal tissues, neural stem cells, embryonic stem cells or other cells and tissues contemplated for neural repair or augmentation. Neural stem/progenitor cells have been described in the art, and their use in a variety of therapeutic protocols has been widely discussed. For example, inter alia, U.S. Pat. Nos. 6,638,501, Bjornson et al.; U.S. Pat. No. 6,541,255, Snyder et al.; U.S. Pat. No. 6,498,018, Carpenter; U.S. Patent Application 20020012903, Goldman et al.; Palmer et al. (2001) Nature 411(6833):42-3; Palmer et al. (1997) Mol Cell Neurosci. 8(6):389-404; Svendsen et al. (1997) Exp. Neurol. 148(1):135-46 and Shihabuddin (1999) Mol Med Today. 5(11):474-80; each herein specifically incorporated by reference.

Neural stem and progenitor cells can participate in aspects of normal development, including migration along well-established migratory pathways to disseminated CNS regions, differentiation into multiple developmentally- and regionally-appropriate cell types in response to microenvironmental cues, and non-disruptive, non-tumorigenic interspersion with host progenitors and their progeny. Human NSCs are capable of expressing foreign transgenes in vivo in these disseminated locations. A such, these cells find use in the treatment of a variety of conditions, including traumatic injury to the spinal cord, brain, and peripheral nervous system; treatment of degenerative disorders including Alzheimer's disease, Huntington's disease, Parkinson's disease; affective disorders including major depression; stroke; and the like. By providing synaptogenesis enhancers, the functional connections of the neurons are enhanced, providing for an improved clinical outcome.

Among the conditions of interest for the present methods of decreasing synaptogenesis are epilepsy, and drug addition. Such conditions benefit from administration of SPARC or Hevin antagonists, which decrease, or inhibit, the development of synapses.

Epilepsy is a recurrent, paroxysmal disorder of cerebral function characterized by sudden, brief attacks of altered consciousness, motor activity, sensory phenomena, or inappropriate behavior caused by excessive discharge of cerebral neurons. Manifestations depend on the type of seizure, which may be classified as partial or generalized. In partial seizures, the excess neuronal discharge is contained within one region of the cerebral cortex. In generalized seizures, the discharge bilaterally and diffusely involves the entire cortex. Sometimes a focal lesion of one part of a hemisphere activates the entire cerebrum bilaterally so rapidly that it produces a generalized tonic-clonic seizure before a focal sign appears.

Methods of Treatment

Modulating synaptogenesis through administering compounds that are agonists or antagonists of Hevin, including Hevin or SPARC polypeptides and fragments thereof is used to promote an improved outcome from ischemic cerebral injury, or other neuronal injury, by modulating synaptogenesis and cellular changes that promote functional improvement. The methods are also used to enhance synaptogenesis in patients suffering from neurodegenerative disorders, e.g. Alzheimer's disease, epilepsy, etc.

Patients can suffer neurological and functional deficits after stroke, CNS injury, and neurodegenerative disease. The findings of the present invention provide a means to enhance synapse formation and to improve function after CNS damage or degeneration. The induction of neural connections induced by promoting synaptogenesis will promote functional improvement after stroke, injury, aging and neurodegenerative disease. The amount of increased synaptogenesis may comprise at least a measurable increase relative to a control lacking such treatment, for example at least a 10% increase, at least a 20% increase, at least a 50% increase, or more.

The Hevin agonists and/or analogs of the present invention are administered at a dosage that enhances synaptogenesis while minimizing any side-effects. It is contemplated that compositions will be obtained and used under the guidance of a physician for in vivo use. The dosage of the therapeutic formulation will vary widely, depending upon the nature of the disease, the frequency of administration, the manner of administration, the clearance of the agent from the host, and the like.

The effective amount of a therapeutic composition to be given to a particular patient will depend on a variety of factors, several of which will be different from patient to patient. Utilizing ordinary skill, the competent clinician will be able to optimize the dosage of a particular therapeutic or imaging composition in the course of routine clinical trials.

Therapeutic agents, e.g. agonists or analogs can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intrathecal, nasal, intracheal, etc., administration. The active agent may be systemic after administration or may be localized by the use of regional administration, intramural administration, or use of an implant that acts to retain the active dose at the site of implantation.

One strategy for drug delivery through the blood brain barrier (BBB) entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB is by intrathecal delivery of therapeutics or imaging agents directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral or intracranial administration include aqueous and non-aqueous, isotonic sterile injection solutions, which can contain antioxidants, buffers, bacteriostats, and solutes that render the formulation isotonic with the blood or cerebrospinal fluid of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g. intravascular (intravenous, intraarterial, intracapillary) administration, injection into the cerebrospinal fluid, intracavity or direct injection in the brain. Intrathecal administration maybe carried out through the use of an Ommaya reservoir, in accordance with known techniques. (F. Balis et al., Am J. Pediatr. Hematol. Oncol. 11, 74, 76 (1989).

Where the therapeutic agents are locally administered in the brain, one method for administration of the therapeutic compositions of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 μl/minute), rather than diffusive flow, to deliver the therapeutic composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing $LD_{50}$ animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g. some agents may be taken for extended periods of time on a daily or semi-daily basis, while more selective agents may be administered for more defined time courses, e.g. one, two three or more days, one or more weeks, one or more months, etc., taken daily, semi-daily, semi-weekly, weekly, etc.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Gene Delivery

One approach for modulating synaptogenesis involves gene therapy. In such methods, sequences encoding Hevin or SPARC or fragments thereof are introduced into the central nervous system, and expressed, as a means of providing Hevin or SPARC activity to the targeted cells. To genetically modify cells that are protected by the BBB, two general categories of approaches have been used. In one type of approach, cells are genetically altered, outside the body, and then transplanted somewhere in the CNS, usually in an area inside the BBB. In the other type of approach, genetic "vectors" are injected directly into one or more regions in the CNS, to genetically alter cells that are normally protected by the BBB. It should be noted that the terms "transfect" and "transform" are used interchangeably herein. Both terms refer to a process which introduces a foreign gene (also called an "exogenous" gene) into one or more preexisting cells, in a manner which causes the foreign gene(s) to be expressed to form corresponding polypeptides.

A preferred approach aims to introduce into the CNS a source of a desirable polypeptide, by genetically engineering cells within the CNS. This has been achieved by directly injecting a genetic vector into the CNS, to introduce foreign genes into CNS neurons "in situ" (i.e., neurons which remain in their normal position, inside a patient's brain or spinal cord, throughout the entire genetic transfection or transformation procedure).

Useful vectors include viral vectors, which make use of the lipid envelope or surface shell (also known as the capsid) of a virus. These vectors emulate and use a virus's natural ability to (i) bind to one or more particular surface proteins on certain types of cells, and then (ii) inject the virus's DNA or RNA into the cell. In this manner, viral vectors can deliver and transport a genetically engineered strand of DNA or RNA through the outer membranes of target cells, and into the cells cytoplasm. Gene transfers into CNS neurons have been reported using such vectors derived from herpes simplex viruses (e.g., European Patent 453242, Breakfield et al 1996), adenoviruses (La Salle et al 1993), and adeno-associated viruses (Kaplitt et al 1997).

Non-viral vectors typically contain the transcriptional regulatory elements necessary for expression of the desired gene, and may include an origin of replication, selectable markers and the like, as known in the art. The non-viral genetic vector is then created by adding, to a gene expression construct, selected agents that can aid entry of the gene construct into target cells. Several commonly-used agents include cationic lipids, positively charged molecules such as polylysine or polyethylenimine, and/or ligands that bind to receptors expressed on the surface of the target cell. For the purpose of this discussion, the DNA-adenovirus conjugates described by Curiel (1997) are regarded as non-viral vectors, because the adenovirus capsid protein is added to the gene expression construct to aid the efficient entry of the gene expression construct into the target cell.

In cationic gene vectors, DNA strands are negatively charged, and cell surfaces are also negatively charged. Therefore, a positively-charged agent can help draw them together, and facilitate the entry of the DNA into a target cell. Examples of positively-charged transfection agents include polylysine, polyethylenimine (PEI), and various cationic lipids. The basic procedures for preparing genetic vectors using cationic agents are similar. A solution of the cationic agent (polylysine, PEI, or a cationic lipid preparation) is added to an aqueous solution containing DNA (negatively charged) in an appropriate ratio. The positive and negatively charged components will attract each other, associate, condense, and form molecular complexes. If prepared in the appropriate ratio, the resulting complexes will have some positive charge, which will aid attachment and entry into the negatively charged surface of the target cell. The use of liposomes to deliver foreign genes into sensory neurons is described in various articles such as Sahenk et al 1993. The use of PEI, polylysine, and other cationic agents is described in articles such as Li et al 2000 and Nabel et al 1997.

An alternative strategy for introducing DNA into target cells is to associate the DNA with a molecule that normally enters the cell. This approach was demonstrated in liver cells in U.S. Pat. No. 5,166,320 (Wu et al 1992). An advantage of this approach is that DNA delivery can be targeted to a particular type of cell, by associating the DNA with a molecule that is selectively taken up by that type of target cell. A limited number of molecules are known to undergo receptor mediated endocytosis in neurons. Known agents that bind to neuronal receptors and trigger endocytosis, causing them to enter the neurons, include (i) the non-toxic fragment C of tetanus toxin; (ii) various lectins derived from plants, such as barley lectin and wheat germ agglutinin lectin; and, (iii) certain neurotrophic factors (e.g., Barde et al 1991). At least some of these endocytotic agents undergo "retrograde" axonal transport within neuron. The term "retrograde", in this context, means that these molecules are actively transported, by cellular processes, from the extremities (or "terminals") of a neuron, along an axon or dendrite, toward and into the main body of the cell, where the nucleus is located. This direction of movement is called "retrograde", because it runs in the opposite direction of the normal outward ("anterograde") movement of most metabolites inside the cell (including proteins synthesized in the cell body, neurotransmitters synthesized by those proteins, etc.).

Compound Screening

In one aspect of the invention, candidate agents are screened for the ability to modulate synaptogenesis, which agents may include candidate Hevin or SPARC derivatives, variants, fragments, mimetics, agonists and antagonists. Such compound screening may be performed using an in vitro cell culture model, a genetically altered cell or animal, or purified protein. A wide variety of assays may be used for this purpose. In one embodiment, compounds that are predicted to be antagonists or agonists of Hevin or SPARC are tested in an in vitro culture system, as described below.

For example, candidate agents may be identified by known pharmacology, by structure analysis, by rational drug design using computer based modeling, by binding assays, and the like. Various in vitro models may be used to determine whether a compound binds to, or otherwise affects Hevin activity. Such candidate compounds are used to contact neurons in an culture environment permissive for synaptogenesis. Such compounds may be further tested in an in vivo model for enhanced synaptogenesis.

Synaptogenesis is quantitated by administering the candidate agent to neurons in culture, and determining the presence of synapses in the absence or presence of the agent. In one embodiment of the invention, the neurons are a primary culture, e.g. of RGCs. Purified populations of RGCs are obtained by conventional methods, such as sequential immunopanning. The cells are cultured in suitable medium, which will usually comprise appropriate growth factors, e.g. CNTF; BDNF; etc. As a positive control, soluble Hevin may be added to certain wells. The neural cells, e.g. RCGs, are cultured for a period of time sufficient allow robust process outgrowth and then cultured with a candidate agent for a period of about 1 day to 1 week, to allow synapse formation. For synapse quantification, cultures are fixed, blocked and washed, then stained with antibodies specific synaptic proteins, e.g. synaptotagmin, etc. and visualized with an appropriate reagent, as known in the art. Analysis of the staining may be performed microscopically. In one embodiment, digital images of the fluorescence emission are with a camera and image capture software, adjusted to remove unused portions of the pixel value range and the used pixel values adjusted to utilize the entire pixel value range. Corresponding channel images may be merged to create a color (RGB) image containing the two single-channel images as individual color channels. Co-localized puncta can be identified using a rolling ball background subtraction algorithm to remove low-frequency background from each image channel. Number, mean area, mean minimum and maximum pixel intensities, and mean pixel intensities for all synaptotagmin, PSD-95, and colocalized puncta in the image are recorded and saved for analysis.

The term "agent" as used herein describes any molecule, e.g. protein or pharmaceutical, with the capability of modulating synaptogenesis, particularly through a Hevin signaling pathway. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Generally a plurality of assay mixtures are run in parallel with different agent concentrations to obtain a differential response to the various concentrations. Typically one of these concentrations serves as a negative control, i.e. at zero concentration or below the level of detection.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of phosphatase inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News,* 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Compounds that are initially identified by any screening methods can be further tested to validate the apparent activity. The basic format of such methods involves administering a lead compound identified during an initial screen to an animal that serves as a model for humans and then determining the effects on synaptogenesis. The animal models utilized in validation studies generally are mammals. Specific examples of suitable animals include, but are not limited to, primates, mice, and rats.

In some embodiments of the invention, a kit is provided, comprising a therapeutic composition for modulation of synaptogenesis, and instructions for use. The therapeutic composition, e.g. a hevin polypeptide, a SPARC polypeptide, or agonist thereof as described herein, may be provided in a unit dose suitable for administration to an individual.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

The number of synapses between CNS neurons in culture is profoundly enhanced by a soluble signal secreted by astrocytes, which is identified herein as Hevin, which is a necessary component of the synapse-promoting activity of astrocyte-conditioned medium. Hevin induces ultrastructurally normal synapses that are presynaptically active but postsynaptically inactive. In vivo, Hevin is concentrated in astrocytes and at synapses throughout the late developing and adult brain. These studies identify Hevin as a soluble synaptogenic protein in the CNS, identify SPARC as its antagonist, and identify astrocytes as important contributors to synaptogenesis within the developing CNS.

Previous studies on synaptogenesis focused mainly on neuronal surface molecules as regulators. It has been particularly difficult to study the role of glia in synaptogenesis in vitro because most CNS neuronal cultures contain glia, which are crucial for neuronal survival. We were able to isolate a pure population of CNS neurons, retinal ganglion cells (RGCs), and culture them in serum-free media of known composition. Using these methods, we have previously shown that RGCs cultured in the presence of astrocytes have 10 times higher levels of synaptic activity than the RGCs cultured alone. This difference has been shown to be due to a 7 fold increase in the number of synapses formed by RGCs cultured with astrocytes or astrocyte conditioned media (ACM). We have previously identified the astrocyte-secreted protein thrombospondin as a signaling molecule that can induce formation of ultrastructurally normal, presynaptically active but postsynaptically silent synapses in RGCs.

The data provided herein demonstrate that two other astrocyte-secreted molecules Hevin (also known as SC1 or SPARC-like 1) and Secreted Protein Acidic and Rich in Cysteine (SPARC, also known as osteonectin) have roles in astrocyte-induced synaptogenesis. Gene expression profiling of astrocytes in developing mouse brain revealed that Hevin mRNA is very highly expressed by astrocytes. Its expression is high during the postnatal period of synaptogenesis and, unlike TSP1 and 2 which are down regulated by maturation, high Hevin mRNA levels are sustained in the adult. In addition to astrocytes, several neuronal populations in the brain and retina including a subpopulation of RGCs and amacrine cells also express Hevin. However, Hevin is not detectable in RGCs in culture by western blotting. Hevin was first identified as a synaptic glycoprotein and has been shown to be localized to CNS synapses.

Figure 1:
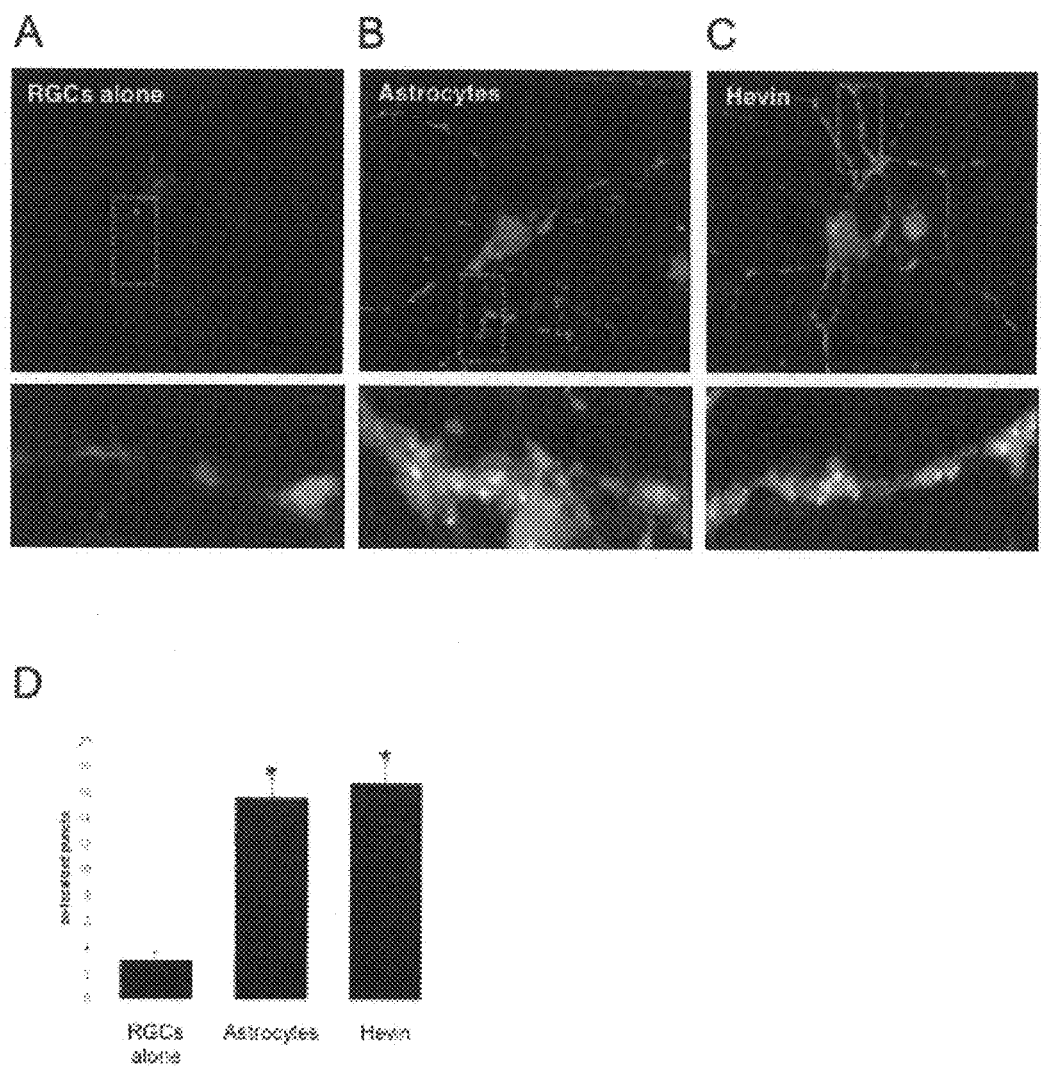
FIGS. 1A-1D: Hevin can induce an increase in the number of synapses made by RGCs. Immunostaining of RGCs for colocalization of presynaptic Synaptotagmin (red) and postsynaptic PSD-95 (green) showed few co-localized synaptic puncta in the absence of astrocytes (A) but many in the presence a feeding layer of astrocytes (B) or 30 nM recombinant Hevin (C). (D) Quantification of the effects of Astrocytes and Hevin on synaptic puncta. Astrocytes and Hevin both significantly increased the number of co-localized synaptic puncta/cell over RGCs alone ($*p<0.05$, n=20, error bars indicate SEM values).

Role of Hevin in CNS synapse formation. We cultured 3 days in vitro (DIV) RGCs alone, with astrocyte feeding layer inserts or in the presence of purified Hevin, using medium as described by Meyer-Franke et al. (1995) Neuron 15(4): 805-19. After an additional 6 DIV with these factors, we co-stained the cells for presynaptic marker Synaptotagmin and postsynaptic marker PSD95 (FIG.1A-C, Synaptotagmin red and PSD95 green). Cells cultured alone had few pre or postsynaptic puncta that mostly did not co-localize indicating that these cells did not form many synapses (FIG.1A). RGCs cultured in the presence of astrocytes or pure Hevin formed many synapses (up to 7 fold more of the synapses formed by RGCs alone, FIGS. 1B, C, and D). We also stained RGCs for two other synaptic markers, Bassoon (pre) and Homer (post), to see whether their co-localization was also increased in RGCs cultured with Hevin. For RGCs cultured with Hevin the number of co-localized Homer and Bassoon puncta was also increased to the same levels as RGCs cultured with astrocytes or TSP (FIG. 2). These data show that purified Hevin is sufficient to increase synapse number inducing clustering and colocalization of pre and post synaptic proteins in RGCs.

Figure 3:
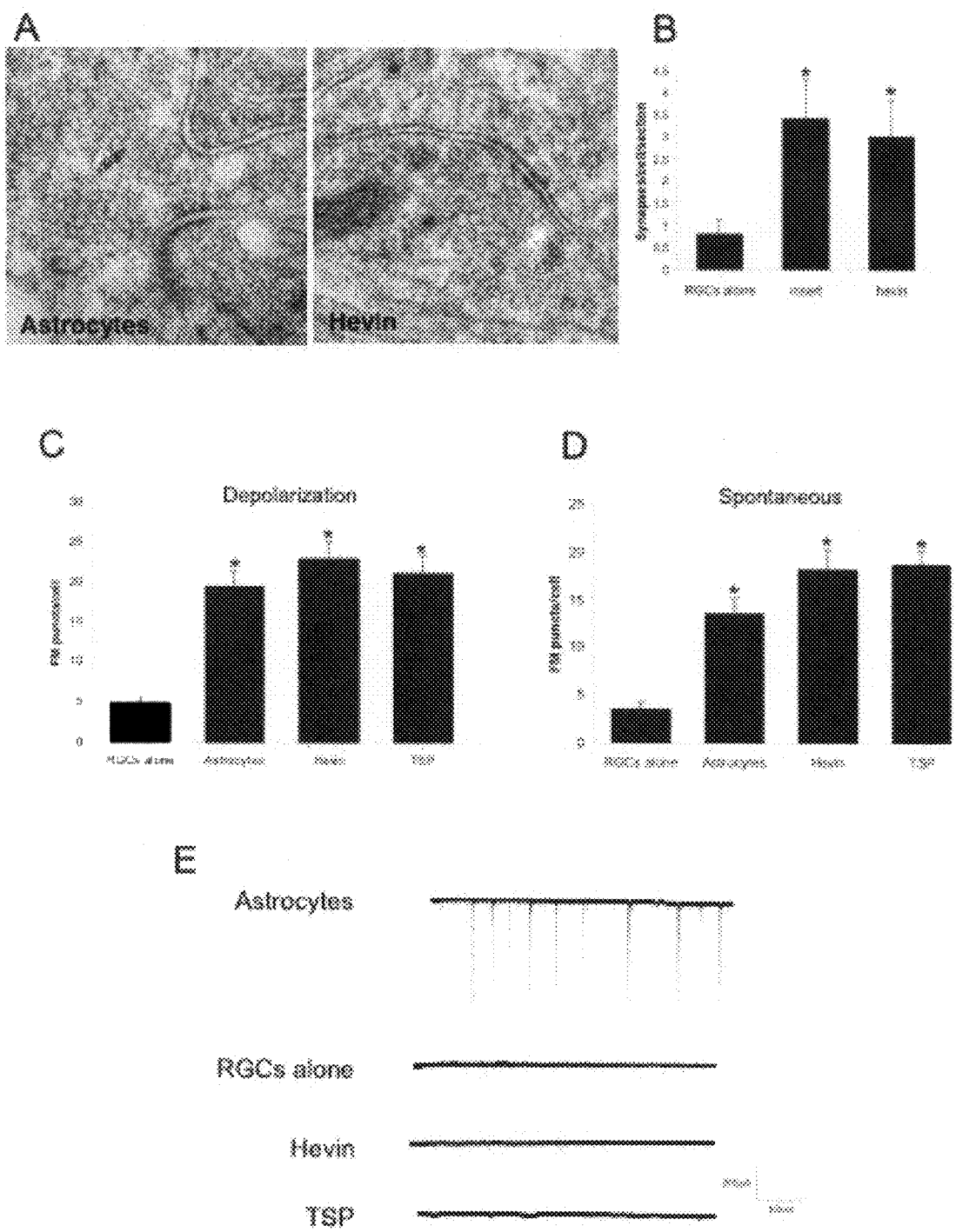
FIGS. 3A-3E: Hevin induces formation of ultrastructurally normal, presynaptically active but postsynaptically silent synapses. (A) Hevin-induced synapses are ultrastructurally normal and resemble astrocyte-induced synapses. (B) Quantification of number of synapses formed by RGCs by EM.

We performed electron microscopy analysis of ultra thin (50 nm) sections of RGCs cultured alone, with astrocytes or Hevin. Synapses formed by Hevin were ultrastructurally identical to the synapses formed by the astrocytes (FIG. 3A), and thus are ultrastructurally normal. We counted the number of synapses per cell (per section) by scanning the cell body and proximal dendrites within a diameter of 3 times that of the cell body. Consistent with the increase in co-localization of pre and post synaptic puncta seen by immunofluorescence, the number of synapses per cell (per section) was 5-7 fold higher in RGCs cultured with Hevin or astrocytes than the RGCs cultured alone (FIG. 3B).

Next, we investigated the pre and post synaptic function of synapses formed by Hevin. To determine whether synapses formed by Hevin were presynaptically active we used a fixable analog of the lipophilic FM dye FM4-64-FX. FM dyes added in to the external media insert into cell membranes and become fluorescent. When the synaptic vesicles are released they are exposed to the external media and the FM dye binds to the membranes. If there is a functional release and recycling machinery, the FM dye will be taken internalized with the recycled synaptic vesicles. We added FM4-64_FX to the external buffer and allowed the dye to be taken by the vesicles through spontaneous presynaptic activity or by KCl induced depolarization. We then washed off the dye on the cell surface and fixed the cells. Internalized FM4-64-FX was imaged and FM-puncta per cell were quantified. Hevin induced synapses were presynaptically active as the RGCs treated with Hevin could uptake FM4-64-FX to the same levels as RGCs cultured with astrocytes or TSP (FIGS. 3C and D). To see whether Hevin-induced synapses were postsynaptically active we performed whole cell patch clamp recordings on RGCs cultured with Hevin (FIG. 3E). Similar to TSP, Hevin synapses were postsynaptically silent. These data show that synapses formed by Hevin are ultrastructurally normal, presynaptically active and postsynaptically silent.

Figure 4:
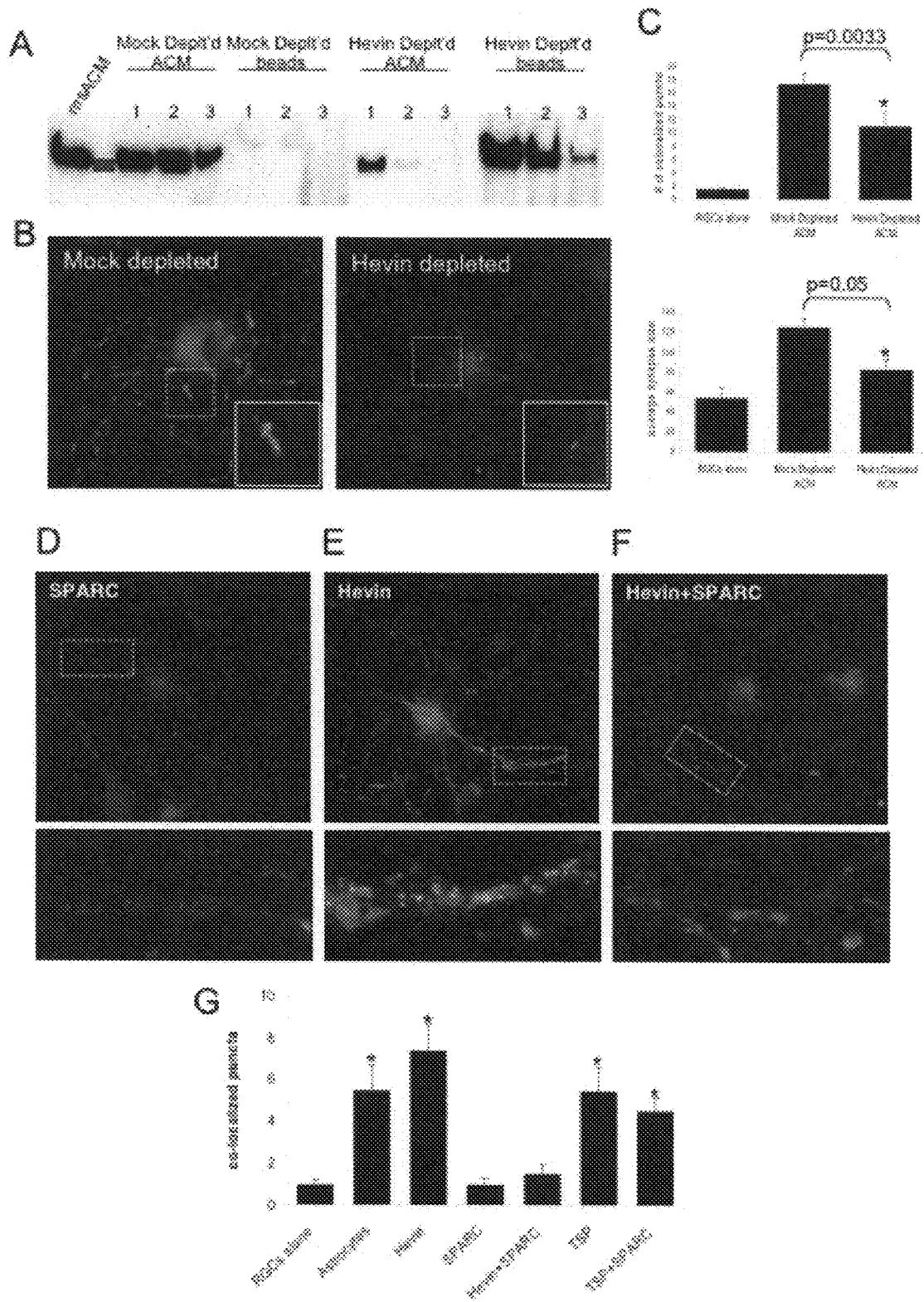

We cultured RGCs with Hevin-depleted ACM and compared the number of synapses formed to the mock-depleted ACM. Hevin depletion led to a 40% decrease in synapse number, but most interestingly, the synapses formed by Hevin-depleted ACM were smaller in size, mostly due to a decrease in the presynaptic puncta size and number (FIG. 4A-C). In addition, the staining pattern suggested that Hevin depletion led to a decrease in the contact of presynaptic puncta with RGC cell bodies and proximal dendrites, suggesting a role for Hevin in the establishment of the axon-dendrite interaction (FIG. 4B). Hevin depleted ACM still contains TSP. Therefore, the remaining synaptogenic activity of the ACM after Hevin depletion can be explained by presence of TSP. However, we have previously seen an almost complete loss of synaptogenic effect of ACM upon TSP depletion indicating that TSP was responsible for the synaptogenic effect of ACM. In addition, despite the lack of double-labeled synaptic puncta in RGCs cultured with TSP depleted ACM, there was still a significant increase in the number of single-labeled puncta containing non-overlapping Synaptotagmin or PSD-95 immunoreactivity. These results suggested that TSP might normally enhance synaptogenesis by inducing or maintaining the alignment and/or adherence of pre- and postsynaptic specializations. The presence of Hevin in the TSP depleted media and the lack of Hevin's compensation for TSP depletion suggested the presence of a third factor in the ACM that was inhibitory to Hevin's synapse forming activity. SPARC is a homolog of Hevin that is also expressed by astrocytes and is present at high levels in ACM. Unlike Hevin, SPARC did not promote synapse formation on RGCs (FIG. 4D). Interestingly, cells treated with SPARC showed an increase in the number of single-labeled puncta with post synaptic PSD-95 immunoreactivity while presynaptic Synaptotagmin was not clustered.

SPARC antagonism of Hevin-induced synaptogenesis. When we added SPARC with Hevin, the synaptogenic activity of Hevin was diminished (FIGS. 4E and F). Interestingly, immunoreactivity for presynaptic Synaptotagmin and postsynaptic PSD95 was high in these cultures (FIG. 4F). In addition, presynaptic Synaptotagmin puncta were excluded from the cell bodies and proximal dendrites, indicating that SPARC interfered with the establishment of axon dendrite contact by Hevin (FIG. 4F). To investigate whether the antagonistic activity of SPARC was specific to Hevin or SPARC could also inhibit TSP induced synapse formation, we co-cultured RGCs with TSP and SPARC. SPARC did not antagonize TSP showing that its inhibitory effect is specific to Hevin-induced synaptogenesis (FIG. 4G). Taken together these results demonstrate that SPARC present in the ACM antagonizes the major synaptogenic effect of Hevin. Thus, due to the inhibitory effect of SPARC, the predominant synaptogenic factor in ACM is TSP. These findings also point out a regulatory role for SPARC in Hevin-induced synaptogenesis and explains the near to total loss of synaptic effect of ACM upon TSP depletion.

Molecular basis of Hevin's synaptogenic activity. To identify the determinants of Hevin-induced synaptogenesis, we investigated which part of Hevin is able to induce synapse formation. Hevin and SPARC have similar domain structures. They share 60% homology at the C-terminal SPARC like domain, and both have a Kazal-like and a follistatin like domain in the middle. Hevin has a long acidic N-terminal domain which is unique to this protein. SPARC only has a short acidic stretch at the N terminal part (FIG. 5A). To find out which part of Hevin is synaptogenic, we subcloned full length Hevin and its truncation constructs (FIG. 5A) into a mammalian expression vector. All the constructs contained an N-terminal signal peptide for secretion and C-terminal myc and 6 Histidine tags. The constructs were transfected into HEK293 cells and the cell conditioned media were tested for the presence of the recombinant proteins (FIG. 5B). The C-terminal truncation construct that lacked the follistatin-like repeat (CΔFollistatin) was not secreted as well as the other constructs and was mostly trapped inside the cells; therefore, we discontinued using this construct. We purified the recombinant proteins from conditioned media (higher than 95% purity by silver staining). 3DIV RGCs were then treated with 30 nM of Hevin or Hevin truncation constructs for 6 additional days and synapse number was determined by Synaptotagmin and PSD95 costaining. The Hevin construct containing the N terminal acidic part plus the follistatin-like domain (N+Follistatin) significantly increased synapse number and mimicked the effect of full length Hevin to a great extent indicating that the synaptogenic activity of Hevin lies within this part of the protein (FIG. 5C).

Hevin and SPARC effects on neruonal survival and neurite outgrowth. SPARC has previously been shown to have neurotrophic and neurite outgrowth promoting properties Therefore, we tested whether Hevin also increased RGC survival and neurite outgrowth. When RGC survival was tested in the absence of any other survival factors in minimal media, Hevin significantly promoted survival of RGCs up to 30%, comparable to the effects of BDNF, CNTF and SPARC (FIG. 6A). This activity reached its maximum at 30 nM range. Interestingly, the survival activity of Hevin or SPARC were not additive to that of the RGC growth media which contained BDNF, CNTF and insulin as survival factors (FIG. 6B). In addition, when we tested the effect of Hevin's domains on RGC survival we saw an effect on RGC survival with the C-terminal part of Hevin, a construct that is not able to induce synapse formation (FIG. 6C). Thus, it is unlikely that Hevin's synaptogenic activity is linked to its neurotrophic function.

Similar to SPARC, Hevin also promotes neurite outgrowth and branching (FIGS. 7A and B). The neurite outgrowth-promoting activity of Hevin was shared by N+follistatin and C+follistatin constructs which suggests that the outgrowth function of Hevin is dependent on the follistatin-like repeat (FIGS. 7A and B). These data show that the synaptogenic function of Hevin can be dissected from its survival and outgrowth effects. In addition, we show that Hevin is a potent neurotropic and neurite outgrowth-promoting factor.

Figure 8:
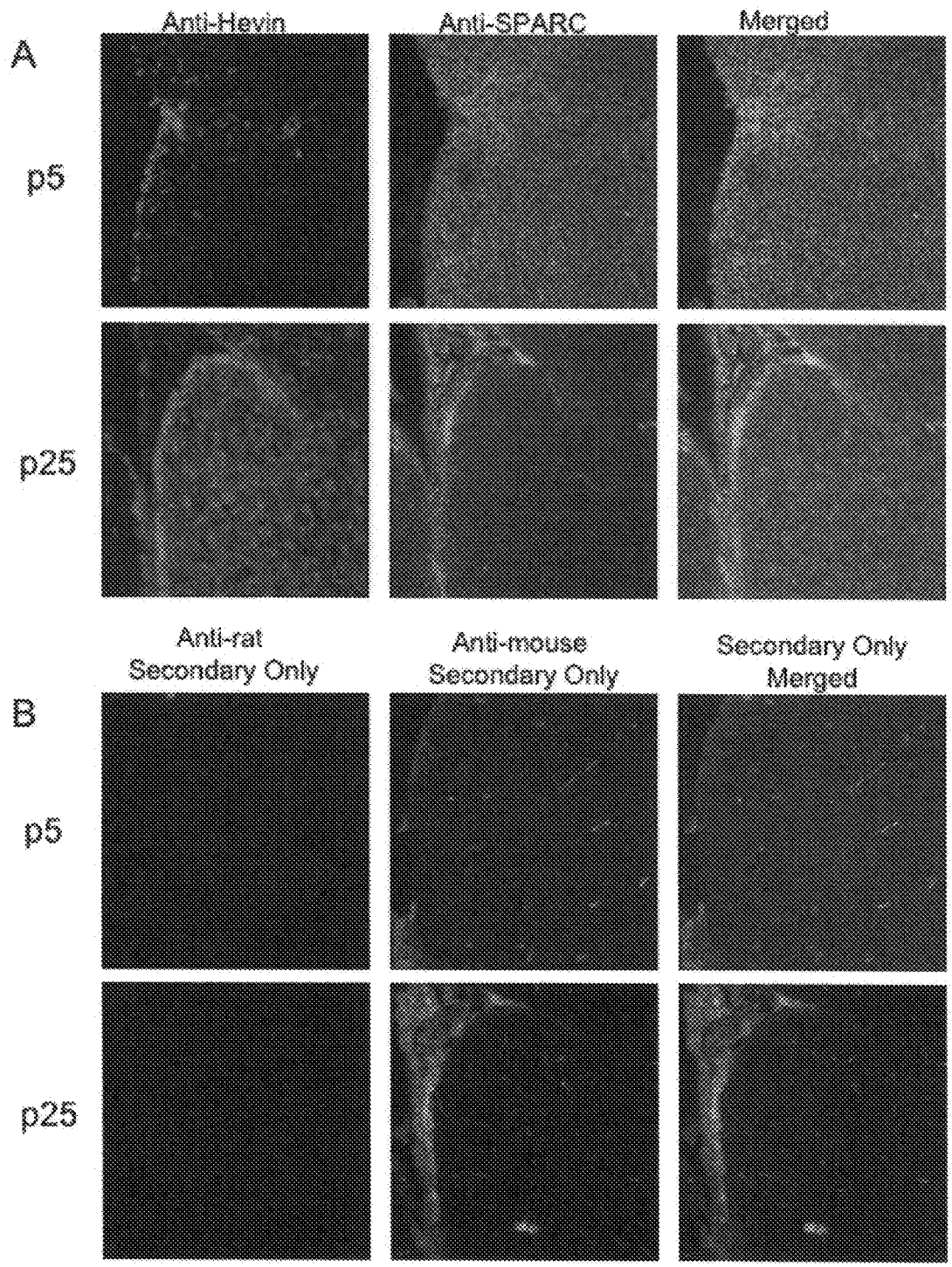

Role of extracellular matrix (ECM) in the formation and stability of central nervous system (CNS) synapses. Our in vitro data raise the question of whether glia regulate synapse formation in vivo through relative SPARC and Hevin amounts. It is known that by embryonic day 16 RGC axons reach their targets in the superior colliculus (SC), yet form very few synapses, until around the end of the first postnatal week. To determine whether there is a correspondence between timing of synapse formation in the SC and the relative expression of Hevin and SPARC, we immunostained cryosections of the SC at various times during development (FIG. 8). We observed a modest Hevin expression and a very strong SPARC signal in the SC at postnatal day 5 (p5), when the bulk of synapses are not yet formed (FIG. 8A, upper panels). By postnatal day 25 (p25), after the synaptic development of this part of the brain is complete, SC showed a very high Hevin expression. Conversely, SPARC expression in this area of the brain was mostly gone by p25 (FIG. 8A, lower panels).

At the neuromuscular junction extracellular matrix proteins such as agrin, dystroglycan and laminin play crucial roles in the formation and stability of synapses. However, many of these proteins are not widely expressed in the CNS or they have been shown to be dispensable for CNS synaptogenesis. Our in vitro findings and correlation of in vivo expression patterns of Hevin and SPARC indicates that these astrocyte-secreted ECM proteins play an important role in the synapse formation in the CNS.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

What is claimed is:

1. A method of enhancing synaptogenesis in an individual with glaucoma comprising the step of:
   contacting a retinal ganglion cell in an individual with glaucoma with an effective dose of a SEQ ID NO:1 polypeptide; wherein the number of synapses is increased in said retinal ganglion cell relative to a retinal ganglion cell that is not contacted with a SEQ ID NO:1 polypeptide.

2. The method of claim 1, wherein the SEQ ID NO:1 polypeptide comprises residues 16-431 of SEQ ID NO:1.

3. The method of claim 1, further comprising administration of neural progenitors.

4. The method of claim 1, wherein the increased number of synapses is measured as a recovery of sensory abilities.

* * * * *